(12) United States Patent
Hoon

(10) Patent No.: US 11,160,542 B2
(45) Date of Patent: Nov. 2, 2021

(54) COLLECTOR FOR DETECTION AND REVERSIBLE CAPTURING OF CELLS FROM BODY FLUIDS IN VIVO

(71) Applicant: Haimachek, Inc., Santa Monica, CA (US)

(72) Inventor: Dave S. B. Hoon, Santa Monica, CA (US)

(73) Assignee: Haimachek, Inc., Santa Monica, CA (US)

( * ) Notice: Subject to any disclaimer, the term of this patent is extended or adjusted under 35 U.S.C. 154(b) by 0 days.

(21) Appl. No.: 15/619,229

(22) Filed: Jun. 9, 2017

(65) Prior Publication Data
US 2017/0354400 A1 Dec. 14, 2017

Related U.S. Application Data

(60) Provisional application No. 62/348,103, filed on Jun. 9, 2016.

(51) Int. Cl.
*A61B 10/00* (2006.01)
*A61M 25/09* (2006.01)
(Continued)

(52) U.S. Cl.
CPC .......... *A61B 10/04* (2013.01); *A61B 1/00016* (2013.01); *A61B 1/00156* (2013.01);
(Continued)

(58) Field of Classification Search
CPC .......... A61B 10/0045; A61B 5/14503; A61M 25/09; A61M 25/09108;
(Continued)

(56) References Cited

U.S. PATENT DOCUMENTS 2,963,850 A * 12/1960 Rosenblatt ............ B21F 45/006
57/258
4,444,744 A 4/1984 Goldenberg
(Continued)

FOREIGN PATENT DOCUMENTS

| CN | 102573655 | 7/2012 |
|---|---|---|
| CN | 103908306 | 7/2014 |

(Continued)

OTHER PUBLICATIONS

PCT Search Report and Written Opinion in PCT/US2017/036824 dated Sep. 7, 2017 in 8 pages.
(Continued)

*Primary Examiner* — David J. McCrosky
(74) *Attorney, Agent, or Firm* — Knobbe, Martens, Olson & Bear, LLP

(57) ABSTRACT

A biomaterial collection device can include a wire that includes a functional member including a proximal end, a distal end, a first flat surface and a second flat surface opposing the first surface. The functional member can be configured to fit within a body lumen. The functional member can include binding elements configured to bind circulating biomolecules and cells. The functional member can include curved portions that form revolutions around the longitudinal axis of the device.

16 Claims, 18 Drawing Sheets

(51) Int. Cl.
  *A61B 10/04*  (2006.01)
  *A61B 5/157*  (2006.01)
  *A61B 1/00*  (2006.01)
  *A61F 2/04*  (2013.01)
  *B21F 45/00*  (2006.01)
  *B21F 7/00*  (2006.01)
  *B21F 3/02*  (2006.01)
  *A61B 34/30*  (2016.01)
  *A61B 17/00*  (2006.01)
  *A61M 37/00*  (2006.01)

(52) U.S. Cl.
  CPC .......... *A61B 5/157* (2013.01); *A61B 10/0045* (2013.01); *A61F 2/04* (2013.01); *A61B 2017/00022* (2013.01); *A61B 2017/00345* (2013.01); *A61B 2034/301* (2016.02); *A61B 2034/303* (2016.02); *A61M 37/00* (2013.01); *A61M 2025/09183* (2013.01); *B21F 3/02* (2013.01); *B21F 7/00* (2013.01); *B21F 45/008* (2013.01); *G01N 2333/705* (2013.01); *G01N 2800/00* (2013.01)

(58) Field of Classification Search
  CPC ... A61M 2025/09175; A61M 25/09183; B21F 3/00; B21F 17/00; B21F 45/008; C12M 1/16; C12M 1/26; C12M 1/263–268; C12M 1/28; C12M 1/32; C12M 45/22; C12M 33/00; C12M 33/06; G01N 2333/705; G01N 2800/00
  See application file for complete search history.

(56) References Cited

U.S. PATENT DOCUMENTS

| | | | |
|---|---|---|---|
| 4,650,547 A | 5/1987 | Gough | |
| 4,854,330 A * | 8/1989 | Evans, III | A61M 25/09 600/585 |
| 4,984,581 A * | 1/1991 | Stice | A61M 25/09 600/434 |
| 5,001,051 A | 3/1991 | Miller et al. | |
| 5,424,187 A | 6/1995 | Shor et al. | |
| 5,804,453 A | 9/1998 | Chen | |
| 5,859,937 A | 1/1999 | Nomura | |
| 5,938,595 A | 8/1999 | Glass et al. | |
| 5,981,297 A | 11/1999 | Baselt | |
| 6,214,560 B1 | 4/2001 | Yguerabide et al. | |
| 6,235,473 B1 | 5/2001 | Friedman et al. | |
| 6,251,142 B1 | 6/2001 | Bernacca et al. | |
| 6,256,522 B1 | 7/2001 | Schultz | |
| 6,379,622 B1 | 4/2002 | Polak et al. | |
| 6,405,066 B1 | 6/2002 | Essenpreis et al. | |
| 6,449,507 B1 | 9/2002 | Hill et al. | |
| 6,465,177 B1 | 10/2002 | Hoon | |
| 6,468,657 B1 | 10/2002 | Hou et al. | |
| 6,488,704 B1 | 12/2002 | Connelly et al. | |
| 6,630,355 B1 | 10/2003 | Pivarnik et al. | |
| 6,630,356 B1 | 10/2003 | Armstrong et al. | |
| 6,649,143 B1 | 11/2003 | Contag et al. | |
| 6,656,702 B1 | 12/2003 | Yugawa et al. | |
| 6,664,111 B2 | 12/2003 | Bentsen et al. | |
| 6,673,596 B1 | 1/2004 | Sayler et al. | |
| 6,673,914 B1 | 1/2004 | Hoon | |
| 6,689,603 B2 | 2/2004 | Pompidou et al. | |
| 6,706,232 B2 | 3/2004 | Hasegawa et al. | |
| 6,721,582 B2 | 4/2004 | Trepagnier et al. | |
| 6,743,639 B1 | 6/2004 | Tondra et al. | |
| 6,746,582 B2 | 6/2004 | Heller et al. | |
| 6,866,837 B2 | 3/2005 | Reubi et al. | |
| 6,908,740 B2 | 6/2005 | Vandekerckhove et al. | |
| 7,037,332 B2 | 5/2006 | Kutryk et al. | |
| 7,553,625 B2 | 6/2009 | Hoon et al. | |
| 7,892,222 B2 | 2/2011 | Vardi et al. | |
| 7,993,909 B2 | 8/2011 | Hoon et al. | |
| 8,084,246 B2 | 12/2011 | Hoon et al. | |
| 8,152,736 B2 | 4/2012 | Caillat et al. | |
| 8,197,756 B2 | 6/2012 | Pison et al. | |
| 8,529,615 B2 | 9/2013 | Hengerer | |
| 8,569,044 B2 | 10/2013 | Hoon et al. | |
| 8,846,580 B2 | 9/2014 | Pison et al. | |
| 9,072,723 B2 | 7/2015 | Kutryk et al. | |
| 9,125,974 B2 | 9/2015 | Hyde et al. | |
| 9,162,884 B2 | 10/2015 | Hoon et al. | |
| 9,173,602 B2 | 11/2015 | Gilbert | |
| 9,658,125 B2 * | 5/2017 | Gilbert | A61B 10/0045 |
| 9,797,907 B2 | 10/2017 | Goldenberg et al. | |
| 2002/0055111 A1 | 5/2002 | Chen et al. | |
| 2002/0115931 A1 | 8/2002 | Strauss et al. | |
| 2003/0134100 A1 | 7/2003 | Mao et al. | |
| 2003/0134416 A1 | 7/2003 | Yamanishi et al. | |
| 2003/0175818 A1 | 9/2003 | Ross et al. | |
| 2003/0175850 A1 | 9/2003 | Ross et al. | |
| 2003/0178641 A1 | 9/2003 | Blair et al. | |
| 2004/0009584 A1 | 1/2004 | Mitra et al. | |
| 2004/0092825 A1 | 5/2004 | Madar et al. | |
| 2004/0100284 A1 | 5/2004 | Lee et al. | |
| 2004/0191246 A1 | 9/2004 | Connelly et al. | |
| 2005/0153309 A1 | 7/2005 | Hoon et al. | |
| 2006/0025713 A1 | 2/2006 | Rosengart et al. | |
| 2006/0183223 A1 | 8/2006 | King et al. | |
| 2007/0154888 A1 | 7/2007 | Klapproth | |
| 2008/0045986 A1 † | 2/2008 | To | |
| 2008/0275464 A1 † | 11/2008 | Abrams | |
| 2009/0117168 A1 | 5/2009 | Keenan | |
| 2009/0312631 A1 | 12/2009 | Rabinovitz et al. | |
| 2011/0124025 A1 | 5/2011 | Castracane et al. | |
| 2011/0301442 A1 | 12/2011 | Lücke et al. | |
| 2012/0116383 A1 | 5/2012 | Mauch et al. | |
| 2012/0191099 A1 | 7/2012 | Victor | |
| 2012/0237944 A1 | 9/2012 | Lücke et al. | |
| 2013/0079663 A1 | 3/2013 | Caillat et al. | |
| 2013/0150707 A1 | 6/2013 | Cima et al. | |
| 2013/0197334 A1 | 8/2013 | Weber et al. | |
| 2013/0282001 A1 | 10/2013 | Hezi-Yamit et al. | |
| 2014/0066729 A1 | 3/2014 | Cosnier et al. | |
| 2014/0206961 A1 | 7/2014 | Hoon et al. | |
| 2014/0322518 A1 | 10/2014 | Addleman et al. | |
| 2014/0357967 A1 | 12/2014 | Lucke et al. | |
| 2014/0367146 A1 * | 12/2014 | Clerkin | B21C 37/045 174/126.1 |
| 2015/0216442 A1 | 8/2015 | Lavy et al. | |
| 2015/0305850 A1 | 10/2015 | Hetts et al. | |
| 2015/0323533 A1 | 11/2015 | Sass et al. | |
| 2016/0007893 A1 | 1/2016 | Roberts | |
| 2016/0007896 A1 | 1/2016 | Hoon et al. | |
| 2016/0135721 A1 | 5/2016 | Bollmann et al. | |
| 2016/0139114 A1 | 5/2016 | Bollmann et al. | |
| 2016/0208389 A1 | 7/2016 | Bollmann et al. | |
| 2016/0216257 A1 | 7/2016 | Nowack | |
| 2016/0313339 A1 | 10/2016 | Goldenberg et al. | |
| 2017/0321261 A1 | 11/2017 | Serrano Fernández et al. | |
| 2017/0354400 A1 | 12/2017 | Hoon | |
| 2018/0008241 A1 † | 1/2018 | Niestroj-Pahl | |

FOREIGN PATENT DOCUMENTS

| | | |
|---|---|---|
| CN | 104546027 | 4/2015 |
| WO | WO 99/341191 | 7/1999 |
| WO | WO 2004/054455 | 7/2004 |
| WO | WO 2005/062940 | 7/2005 |
| WO | WO 2013/176730 | 11/2013 |
| WO | WO 2016/116503 | 7/2016 |

OTHER PUBLICATIONS

Fritz, et al "Electronic detection of DNA by its intrinsic molecular charge," PNAS, vol. 99, No. 22, Oct. 29, 2002, pp. 14142-14146.

Greenberg, et al., "Detection of hepatocyte growth factor/scatter factor receptor (c-Met) in axillary drainage after operations for breast cancer using reverse transcriptase-polymerase chain reaction," Breast Cancer Research, vol. 5, No. 3, pp. R71-R76.

(56) References Cited

OTHER PUBLICATIONS

Russo, "Integrated Silicon Field-Effect Sensors and Microfluidics for Biomolecular Detection," Submitted to the Department of Electrical Engineering and Computer Science, Massachusetts Institute of Technology, Feb. 9, 2004, 60 pages.
Savran, et al., "Micromechanical Detection of Proteins Using Aptamer-Based Receptor Molecules," Analytical Chemistry, p. Est: 4.4, pp. A-E.
Selected Abstracts, New Applications of Cellular and Molecular Technology in Breast Cancer Management, An Unofficial Satellite Event at San Antonio Breast Cancer Symposium, 2003, 14 pages.
Vo-Dinh, et al., "Fiberoptic Immunosensors," Fiber Opt. Chem. Sensors and Biosensors, O.S. Wolfbeis, Ed., vol. 2, Chapter 17, pp. 217-223, CRC Press, Boca Raton, FL, (1991).
Duerig et al., Materials Science and Engineering A273-275, An Overview of Nitinol Medical Applications,1991,p. 149-160.
Scherag et al., Analytical Chemistry, Highly Selective Capture Surfaces on Medical Wires for Fishing Tumor Cells in Whole Blood p. 1846-1854, published Dec. 20, 2016.
EP Extended Search Report in PCT2017/036824 dated Jun. 26, 2020 in 11 pages.
Partial Search Report in PCT/US2017/036824, dated Jan. 22, 2020 in 13 pages.
International Preliminary Report on Patentability in PCT/US2017/036824, dated Dec. 20, 2018 in 5 pages.
Office Action in EP 17811109.2, dated Feb. 15, 2021 in 4 pages.
Office Action in CN 201780047722.4, dated Mar. 17, 2021 in 7 pages.
Frank D. Scherag et al, Analytical Chemistry, Highly Selective Capture Surfaces On Medical Wires For Fishing Tumor Cells In Whole Blood pp. 1846-1854, published Dec. 20, 2016.†
T.Duerig et al., Materials Science And Engineering A273-275, An Overview Of Nitinol Medical Applications, pp. 149-160, published 1999.†

\* cited by examiner
† cited by third party

COLLECTOR FOR DETECTION AND REVERSIBLE CAPTURING OF CELLS FROM BODY FLUIDS IN VIVO

INCORPORATION BY REFERENCE TO ANY PRIORITY APPLICATIONS

This application claims the benefit under 35 U.S.C. § 119(e) as a nonprovisional application of U.S. Prov. App. No. 62/348,103 filed on Jun. 9, 2016, which is hereby incorporated by reference in its entirety. Any and all applications for which a foreign or domestic priority claim is identified in the Application Data Sheet as filed with the present application are hereby incorporated by reference under 37 CFR 1.57.

BACKGROUND

Field of the Invention

The invention relates in some aspects to a collector for biological material including markers.

Description of the Related Art

Several devices exist for in vitro, in vivo, or ex vivo collection and/or detection of biological components, such as cells or other markers. However, several issues such as suboptimal sensitivity and/or specificity exist. As such, there remains a need for improved methods and devices for detecting biological components of disease.

PCT Pub. No. WO2013/176730 to Life Technologies, incorporated by reference in its entirety, teaches a method in which antibodies have been engineered to include a specific protease cleavage site in the hinge region which allows cell release with a specific protease which does not affect the cells significantly. Alternative binding molecules such as scaffold molecules have also been described which overcome some of the limitations of antibodies. These are proteins of small size, single-chain structure, and few post-translational modifications.

Vascular catheters used for medical interventions usually have a cylindrical shape. The advantage of this form is the relatively low frictional resistance. However, this form narrows the flow of blood in small vessels and may increase the risk of thrombosis. U.S. Pat. Pub. No. 2012/0237944 A1 to Luecke et al., incorporated by reference in its entirety, discloses a detection device for the in vivo and/or in vitro enrichment of sample material, in which a functional surface covered with detection receptors has a three-dimensional structure with opposing functional sections forming liquid covered gaps. The individual sections of the functional surface can be equipped with chemically identical or different detection receptors, and the opposing functional sections form liquid covered gaps.

SUMMARY

In some embodiments, disclosed herein is a biomaterial collection device. The collection device can include, for example, a wire that includes a functional member that can include a proximal end, a distal end, a first flat surface and a second flat surface opposing the first surface. The functional member can be configured to fit within a body lumen. The functional member can include binding elements configured to bind circulating biomaterials of interest. The functional member can also include curved portions/windings that form revolutions around the longitudinal axis of the device. In some embodiments, the wire can include from about 3 revolutions to about 5 revolutions per 1 cm of length of the wire, or about 4 revolutions per 1 cm of length of the wire. The wire can be a metal, such as stainless steel or Nitinol in some cases. The probe can also include a proximal handle that does not include binding elements, and an atraumatic distal end. The functional member can also include a third surface and a fourth surface, the third surface and the fourth surface each adjacent the first surface and the second surface. The third surface and the fourth surfaces can be flat surfaces, or not flat (e.g., rounded surfaces), and not contain binding elements in some cases.

In some embodiments, disclosed herein is an in vivo biomaterial collection device, that can include a proximal end, a distal end, a first surface and a second surface opposing the first surface. The functional member can be configured to fit within a body lumen. The functional member can include binding elements configured to bind circulating biomolecules and cells. The functional member can include curved portions that form revolutions around the longitudinal axis of the device; and a collar operably connected to the proximal end of the helical functional member. The collar can be configured to stably position the device within a body lumen. The functional member can have a circular cross-section, or a non-circular, e.g., square or rectangular cross section in some embodiments. The device can also include a filter operably connected to the collar to isolate cells according to their size, such that it can also can change the blood flow. In some embodiments, the binding elements can include fusion proteins, nucleic acids, biological probes, or synthetic material probes. The helical functional member can be coupled to, or be part of a guidewire. The guidewire can include a metallic and/or polymeric material.

In some embodiments, disclosed herein is an in vivo biomaterial collection device. The device can include a functional member that includes a proximal end, a distal end, a first surface and a second surface opposing the first surface. The functional member can be configured to fit within a body lumen. The functional member can include binding elements configured to bind circulating biomolecules and cells. The functional member can also include curved portions that form revolutions around the longitudinal axis of the device. The functional member can be transformable from a first curved configuration to a second configuration more linear than the first configuration. In some embodiments, the second configuration has a greater axial length than the first configuration. The functional member can include a shape memory material. In some embodiments, the device is transformable from the second configuration to the first configuration via exposure to body temperature. The device can also include a plurality of flaps operably connected to the distal end of the functional member. The flaps can include apertures configured to filter blood. The device can also include a control line operably connected to the flaps. The flaps can be movable between a first radially compressed configuration to a second radially expanded configuration. The functional member can include a bifunctionally charged carrier. The control line can run at least partially through one or more eyelets on the functional member, or at least partially through one or more apertures on the functional member.

In some embodiments, disclosed herein is a method for collecting markers associated with disease. The method can include, for example, providing a probe comprising a wire comprising a functional member comprising a proximal end, a distal end, a first flat surface and a second flat surface opposing the first surface, wherein the functional member comprises binding elements configured to bind circulating biomaterials of interest, wherein the functional member comprises curved portions that form revolutions around the longitudinal axis of the device, wherein the binding elements have affixed thereto at least one binding partner for binding a marker, and wherein the binding surface is configured to immobilize a marker to the binding surface upon binding of the marker to the binding partner; positioning at least a portion of the probe in an anatomical structure of a living organism; maintaining the probe in a generally fixed position; and removing the probe from the living organism.

DETAILED DESCRIPTION

Figure 1:
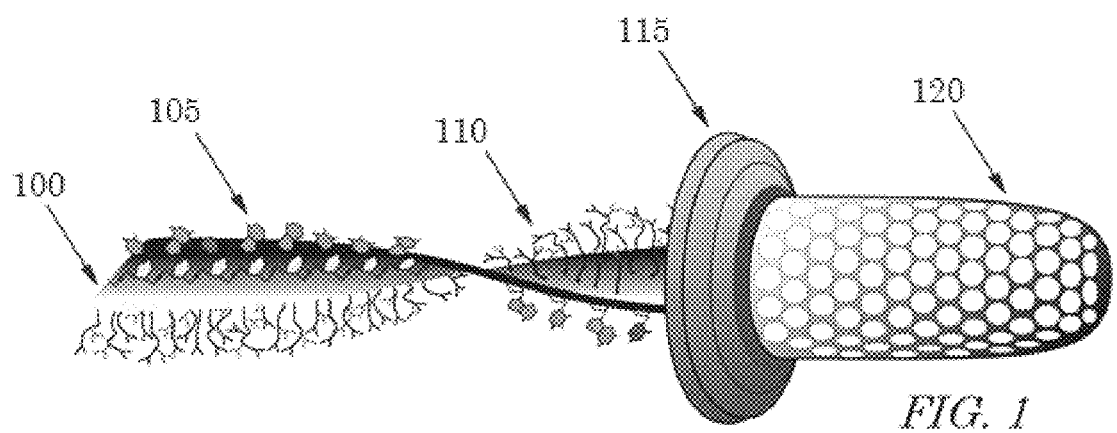
FIG. 1 illustrates a lateral view of one embodiment of an in vivo collector that has a functional surface with a spiral or helical shape and an umbrella-like sieve and collar.

Some embodiments of the present invention generally provides improved devices and methods for detecting and/or reversibly capturing rare cells, molecules, tumor markers, and other biomaterials from body fluids in vitro, ex vivo, or in vivo over time. Embodiments of the invention include a collector device configured for placement within a living organism (or in vitro using a sample from a living organism) for a period of time to provide sufficient yield of biological markers from any body fluid for analysis.

In some embodiments, the functional surface has a first, substantially linear configuration for insertion into a body lumen, such as an artery or vein for example. Upon contact with blood (e.g., at a higher temperature than room temperature) the functional surface which can include a shape memory material can transform to a second, substantially nonlinear configuration, such as a coiled configuration, which can advantageously have an increased surface area for retaining cells or other markers of interest. The coiled configuration can have an axial length that it shorter than that of the substantially linear configuration in some embodiments, similar to that of a compressed and extended spring. After the in-vivo application the wire can be rotated back or thru a temperature change to its original form, such as a rectangular wire form. Now the rare cells on the wire can be immunostained fluorescently labeled and the target cell can be identified, quantified and enumerated under a fluorescence microscope or related type reader on or off the wire. Subsequent statistical analysis enables reviewers to obtain potential diagnostic information.

In some embodiments, disclosed herein is an in vivo biomaterial collection device. The device can include, for example, a functional member comprising a proximal end, a distal end, a first surface and a second surface opposing the first surface. The functional member can be configured to fit within a body lumen. The functional member can include binding elements configured to bind circulating biomolecules and cells. The functional member can also include curved portions that form revolutions around the longitudinal axis of the device. The device can also include a collar operably connected to the proximal end of the helical functional member, the collar configured to stably position the device within a body lumen. The functional member can have a variety of cross-sections, including a circular, non-circular, square, or rectangular cross-section, for example. The device can also include a filter operably connected to the collar to isolate cells according to their size it also can change the blood flow. The binding elements can include fusion proteins, biological probes, and/or synthetic material probes. The helical functional member can be coupled to a guidewire, which can include a metallic and/or polymeric material, for example.

Also disclosed herein is an in vivo biomaterial collection device. The device can include a functional member that includes a proximal end, a distal end, a first surface and a second surface opposing the first surface. The functional member can be configured to fit within a body lumen. The functional member can include binding elements configured to bind circulating biomolecules and cells. The functional member can also include curved portions that form revolutions around the longitudinal axis of the device. The functional member can be transformable from a first curved configuration to a second configuration more linear than the first configuration. In some embodiments, the second configuration has a greater axial length than the first configuration. The functional member can include a shape memory material. The device can be transformable from the second configuration to the first configuration via exposure to body temperature. The device can also include a plurality of flaps operably connected to the distal end of the functional member. The flaps can include apertures configured to filter blood. The device can also include a control line operably connected to the flaps. The flaps can be movable between a first radially compressed configuration to a second radially expanded configuration. The functional member can include a bifunctionally charged carrier. The control line can run at least partially through one or more eyelets, or apertures, on the functional member.

The devices, systems and methods described within this disclosure are, in some embodiments, generally for detecting and/or reversibly capturing cells, nucleic acids, biomolecules, and other biomaterials from body fluids (blood, csf, bone marrow, peritoneal/pleural cavity, bladder) in vivo over time. The captured material can then be analyzed for scientific or diagnostic purposes. In some embodiments, the devices and methods described herein may be used for the early detection of occult cancer cells, infections, or other disease markers. However, they may also be used to detect, capture, or monitor any cell type or biomarker in any body fluid. As will be described below, some embodiments of devices and methods in this disclosure provide an in vivo collecting device that allows safer and more efficient detection and collection of rare cells and biomaterials from body fluids. The devices can also be used ex vivo or in vitro in some embodiments. In some embodiments, the in vivo collecting device includes a spiral, helical, or conical shaped functional surface, which may enhance cell or biomarker binding from the blood while decreasing the risk of thrombosis. Not to be limited by theory, a spiral or helical flow of blood may decrease the concentration of platelets near the vessel wall, thereby reducing the risk of intravascular thrombosis. This effect could be synergistically improved by utilization of a flat wire or other surface, as disclosed elsewhere herein. In some embodiments, the in vivo collecting device includes binding proteins on the functional surface that allow gentle cell release combined with specific binding and simple engineering.

FIG. 1 illustrates one embodiment of an in vivo collecting device shown as it would sit inside a vein, artery, or another body lumen. In this embodiment, the device may have one, two, or more functional surfaces with a spiral or helical shape 100. In some embodiments, a spiral or helical shape is defined by a curve that is the locus of a point that rotates about a fixed point while continuously increasing its distance from that point. In some embodiments, the functional surface may have a coiled shape. The number of coils may be varied. The coil structure may be formed linear or conical. The number of helices and the pitch may be variable. In some embodiments of the device, the diameter of the functional surface may be variable between about 0.3 mm and about 5 mm. The number of windings may vary with the length and pitch of the coil. The diameter (or height or width) of the wire material may be, in some embodiments, variable between about 0.1 mm and 1.0 mm. The thickness of the wire may also change within the structure in order to vary the fluid dynamics within the range of the whole structure. If the shape of the functional surface is conical, the structure may vary in length between, for example, 1 cm and 5 cm. The coil pitch may be adjusted to gain a variable diameter between the windings. In some embodiments, the functional surface may have a shape other than spiral, helical, or conical. In some embodiments, the detection area is coated with a biocompatible coating with protein repellent properties. The coating may include, for example, synthetic (e.g. Polycarboxylate brush structures) or natural (e.g. alginate) polymers that form a hydrogel or brush like structures.

Figure 2:
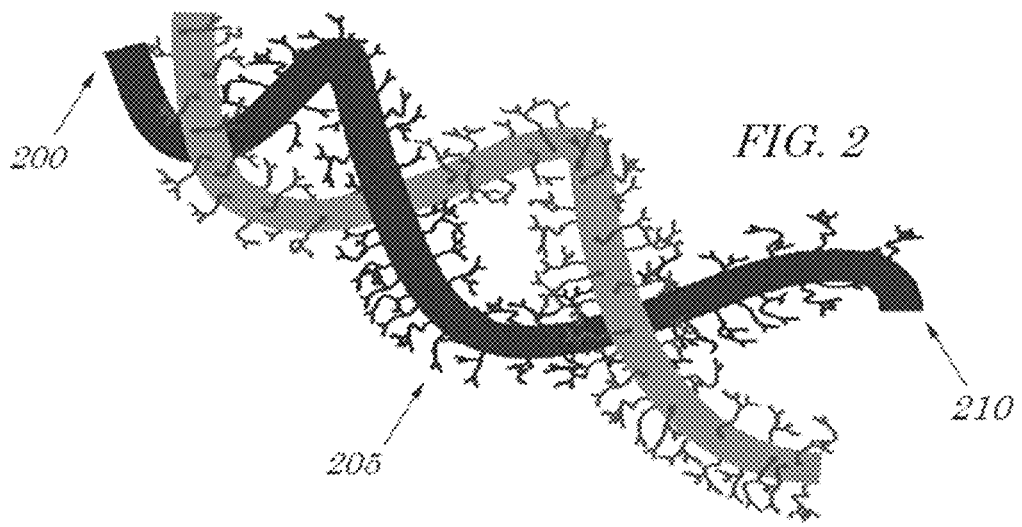
FIG. 2 illustrates a lateral view of one embodiment of the functional surface of an in vivo collector, which has a helical or conical shape.

FIG. 2 illustrates one embodiment of the functional surface of the collection device that may include a coil 210 that is formed into a conical shape. Detection molecules that bind rare cells or other biomarkers 205 may be operably connected to the coil. In some embodiments, the narrow end of the spiral 200 is oriented in the direction of the blood stream, which results in the bloodstream and its circulating cells (CTC, circulating endothelial cells (CEC), stem cells, specific normal cells from organs), which can be rare, being slowed down.

The functional surface of the device may feature detection biomolecules that are operably connected to its surface 105 and 110. The detection molecules may be designed to bind rare cells, nucleic acids, exosomes, and/or other biomarkers. The detection molecules may be of one, two, or more types. The detection molecules may be antibodies or other proteins or nucleic acid or synthetic/natural mimics of all.

In some embodiments, the detection device may have an umbrella-like collar 115, such as proximal or distal to the functional surface of the device. The collar 115 can be radially expandable, and may permit adjustment of the device to the diameter of a blood vessel or other body lumen to prevent migration of the detection device. In some embodiments, the detection device may have an umbrella-like sieve 120 positioned, for example, proximal or distal to the collar. In some embodiments, the collar 115 has a funnel shape as shown, with a decreasing diameter from a proximal to a distal end to direct flow into the sieve 120. The collar 115 can have a central lumen to allow fluid flow therethrough. In some embodiments, the functional surface 100, which can be a wire in some embodiments, can be operably attached to the collar 115 at its proximal end, and fluid can flow in one or more openings around the attachment to the collar 115. The sieve 120 can be operably attached at its proximal end to the distal end of the collar 115. In some embodiments, the sieve 120 can also serve as a functional surface to bind materials of interest. In some embodiments, the sieve 120 has apertures to allow for flow through the sieve 120 while being able to trap some materials of interest within the sieve 120.

Figure 3:
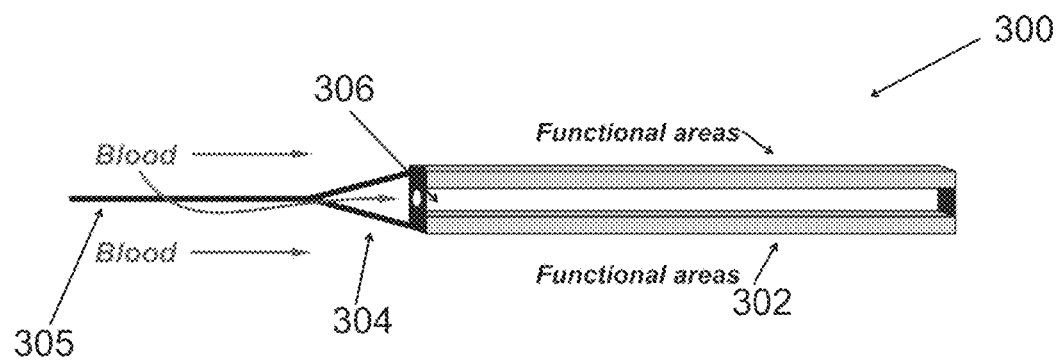
FIG. 3 illustrates various views of an embodiment of an in vivo collector having a flattened, e.g., flat wire.

FIG. 3 illustrates another schematic embodiment of a detection device 300 having a rectangular or square cross-section partially or completely along the axial length of the elongate functional surface. The device 300 can also include one, two, or more lumens, such as central lumen 306 to allow blood to flow therethrough, the sidewall of the lumen 306 surrounded by functional surfaces 302. In some embodiments, blood can also flow radially outwardly of the outer wall of the functional surfaces 302, and capture of markers, cells, or other materials can occur along the outer wall as well as inside the central lumen. Also illustrated is a tether line 305 with one, two, three, or more distal forked extensions 304 operably connected to the proximal end of the functional surface 302 as illustrated. In some embodiments, the functional element 302 can have a cross-sectional width of about 4 mm, such as between about 1 mm and about 10 mm, between about 2 mm and about 6 mm, or between about 3 mm and about 5 mm, with functional area walls having cross-sectional widths of about 1 mm each, such as between about 0.1 mm and about 5 mm each, or between about 0.5 mm and about 2 mm each.

Some embodiments are directed to enhancements to existing in vivo devices. To the inventors' knowledge, many existing devices are shaped in a round form (circular cross-section) like a biopsy needle. With these devices it can be potentially very difficult to do direct immunostaining or visualization for characterization of specific captured cells afterwards. Disclosed herein, in some aspects, are imaging target components on an in-vivo detector.

In some embodiments, a device includes a "flat" medical wire, configured after the functionalization of the flat wire it can rotate 360 degrees about the central axis of the wire and the length of the wire, as illustrated for example in FIG. 3. In some embodiments, the wire does not have a circular cross-section, but rather can be oval or ellipsoid in some embodiments. In some embodiments, a "flat" wire can include a substantially square or rectangular cross-section partially or entirely along the length of the functional surface. In some embodiments, the wire can have a length, a width, and a thickness, wherein the width is about or at least about 1.5×, 2×, 2.5×, 3×, 3.5×, 4×, 4.5×, 5×, 6×, 7×, 8×, 9×, 10×, or more (or ranges incorporating any two of the aforementioned values) relative to the thickness of the wire at a selected cross-section transverse to the longitudinal axis of the wire. In some embodiments, the wire is solid/has a solid core, that is, it does not include an aperture or central lumen. The number of rotations (which can be 1, 2, 3, 4, 5, 6, 7, 8, 9, 10, or more) can vary depending on the desired clinical result and per a given length (such as windings per cm, for example); this can allow to adapt to different vein blood flow rates, more rotation can mean a reduced flow rate along the medical wire. In some embodiments, the wire can have a first dimension, such as a width, of between about 0.1 mm and about 5 mm, between about 0.25 mm and about 3 mm, between about 0.50 mm and about 3 cmm, between about 0.50 mm and about 2 mm, between about 0.50 mm and about 1.5 mm, between about 1 mm and about 2 mm, between about 0.60 mm and about 1.50 mm, about 0.60 mm, 0.70 mm, 0.80 mm, 0.90 mm, 1.00 mm, 1.10 mm, 1.20 mm, 1.30 mm, 1.40 mm, 1.50 mm, or other ranges incorporating any two of the aforementioned values depending on the desired clinical result. In some embodiments, the wire can have a second dimension, such as a thickness or height, of between about 0.05 mm and about 1 mm, between about 0.05 mm and about 0.5 mm, between about 0.05 mm and about 0.3 mm, between about 0.10 mm and about 0.30 mm, or about 0.10 mm, 0.12 mm, 0.14 mm, 0.16 mm, 0.18 mm, 0.20 mm, 0.22 mm, 0.24 mm, 0.26 mm, 0.28 mm, 0.30 mm, or ranges incorporating any two of the aforementioned values depending on the desired clinical result. Sample non-limiting width and thickness dimensions for a wire can be, in some embodiments, about 0.80 mm×0.15 mm for an in vivo application, or 1.32 mm×0.18 mm for an in vitro flow system application, although other dimensions are also possible as noted above.

In some embodiments, the functional member can include a shape memory material, such as Nitinol or a shape memory polymer, for example. Shape memory materials are smart materials that have the ability to return from a deformed state (temporary shape) to their original (permanent) shape induced by an external stimulus (trigger), such as temperature change. A NiTi shape memory metal alloy can exist in two different temperature-dependent crystal structures (phases) called martensite (lower temperature) and austenite (higher temperature or parent phase). Several properties of austenite NiTi and martensite NiTi are notably different. When martensite NiTi is heated, it begins to change into austenite. The temperature at which this phenomenon starts is called austenite start temperature (As). The temperature at which this phenomenon is complete is called austenite finish temperature (Af). When austenite NiTi is cooled, it begins to change into martensite. The temperature at which this phenomenon starts is called martensite start temperature (Ms). The temperature at which martensite is again completely reverted is called martensite finish temperature (Mf). In some embodiments, the functional surface is coated by one, two, or more polymers, of which one, two, or more binding agents can be attached thereto.

Figure 3A:
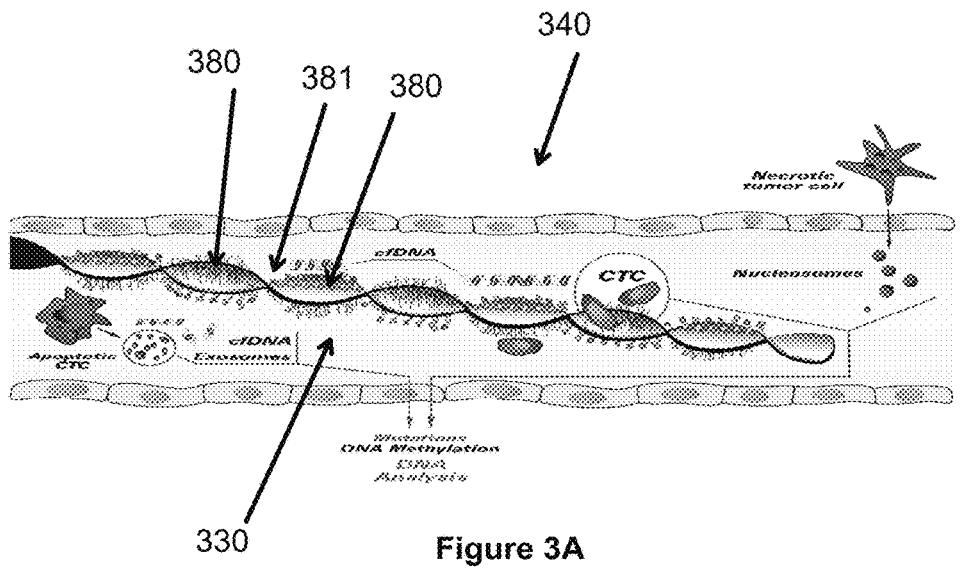
FIGS. 3A-3C illustrate various views of an embodiment of a collector having a flat wire configuration.
Figure 3B:
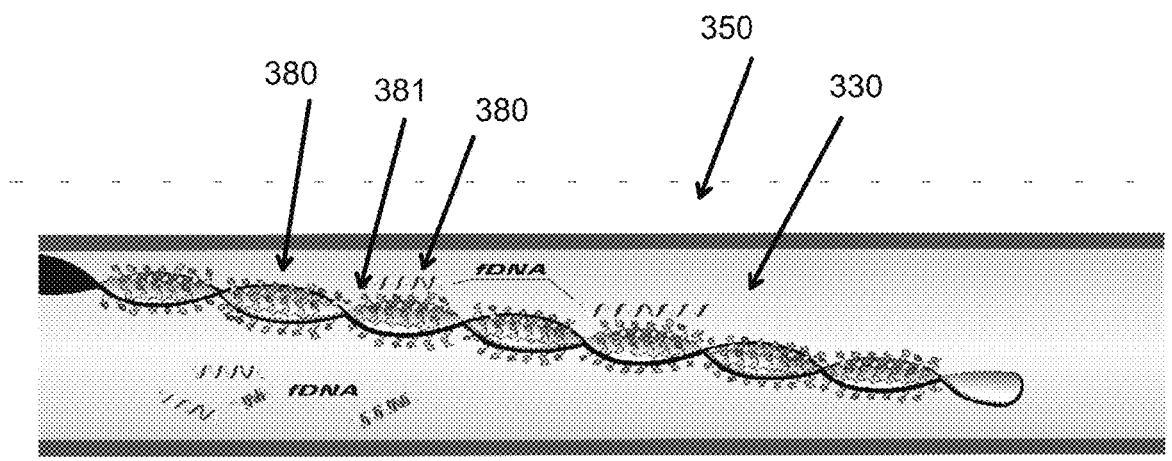

In some embodiments, as shown in FIGS. 3A and 3B, a probe 330 can include a wire that can be a flat wire in some cases. The probe 330 can include a plurality of flat segments 380 interspersed by winding sections 381 as the wire is twisted around itself as shown. The flat segments 380 can be generally parallel to the longitudinal axis 383 of the wire in some embodiments. In some embodiments, the probe can have between about 1 and about 10 windings, between about 1 and about 8 windings, between about 1 and about 6 windings, between about 2 and about 6 windings, between about 3 and about 5 windings, about 4 windings, or about 2, 3, 4, 5, 6, 7, 8, 9, or 10 windings (all of the foregoing with respect to a particular length of the wire, such as per about 1 cm of length of the wire in some embodiments). In some embodiments, the entire probe, the entire functional area of the probe, or a portion of the functional area of the probe can be made of a flat wire that includes a number of windings as disclosed herein. The windings can be regularly and/or irregularly spaced apart in some embodiments. FIG. 3A schematically illustrates a probe 330 within a blood vessel 340 and configured to collect materials of interest, such as circulating tumor cells for example. FIG. 3B schematically illustrates a probe 330 within a urine specimen for collection of, for example, fDNA. The collection can occur, for example in a probe within the bladder such as an indwelling Foley catheter, or completely external to the bladder, such as in a urine specimen container.

In some embodiments, the wire includes between about 12 windings and about 20 windings per 4 cm of length of the wire, such as between about 13 windings and about 19 windings per 4 cm of length of the wire, between about 14 windings and about 18 windings per 4 cm of length of the wire, between about 15 windings and about 17 windings per 4 cm of length of the wire, or about 12, 13, 14, 15, 16, 17, 18, 19, or 20 windings per 4 cm of length of the wire, or ranges incorporating any two of the aforementioned values.

Figure 3C:
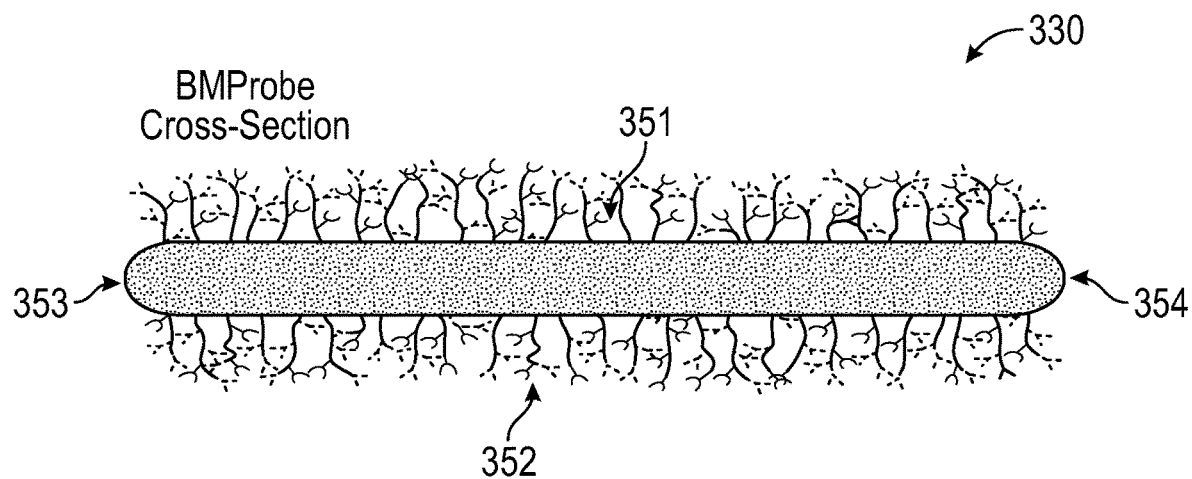

FIG. 3C illustrates a cross-section through a flat segment of the wire 330 of the probe of FIGS. 3A and 3B, according to some embodiments of the invention, with first 351 and second 352 opposing functional surfaces that can be flat or substantially flat as previously described, and parallel or substantially parallel to each other as illustrated. The lateral third 353 and fourth surfaces 354 of the wire can be straight, or rounded as illustrated in some embodiments as shown to be less traumatic to the body lumen of interest. In some embodiments, the lateral third 353 and fourth 354 surfaces can be functional surfaces or non-functional (e.g., do not serve as binding surfaces for material detection or collection). In other words, in some embodiments, less than the entire perimeter of the functional surface of the binding surface serves as a binding surface for materials of interest.

In some embodiments, the binding surface may be configured with an increased surface area to provide an increased number of binding sites on the probe, such as described, for example in U.S. Pat. No. 8,084,246 to Hoon et al., which is hereby incorporated by reference in its entirety. The surface area may be increased by providing an increased longitudinal length, increased diameter or cross-section through at least a portion of the distal zone. In addition, or alternatively, at least a portion of the distal zone may comprise a porous material and/or microstructure to increase the surface area. In some embodiments the binding surface does not include an increased surface area (e.g., lacks pores and/or a microstructure) and can have, for example, a smooth, uninterrupted, and/or continuous surface. In some embodiments, the device includes, or does not include any of the following structures: a spiral, screw-shaped, worm-shaped, undulated, helical, filamentous, brush-like, comb-like, net-like, porous, spongy or similar structures.

Example 1

In some embodiments, experiments were performed to determine the influence of different number of windings on in vitro cell binding. Human umbilical cord endothelial cells (HUVEC) were bound to anti-CD146 coated probes (BM Probe02) in flow system with cell culture medium. The influence of the number of windings on a 4 cm length of a 1 mm flat steel wire was tested.

Figure 3D:
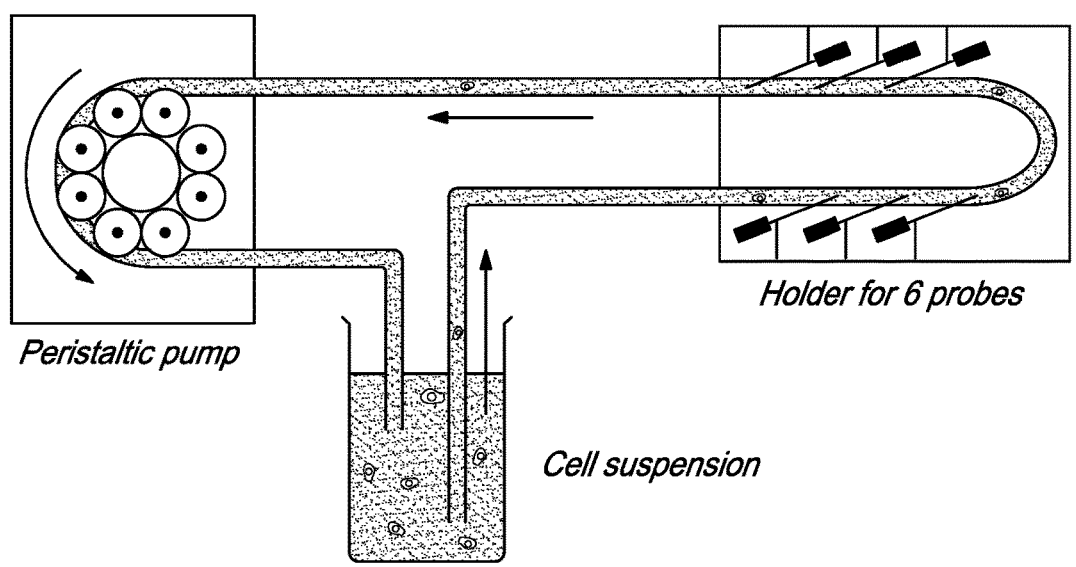
FIGS. 3D-3H illustrate experimental data and a testing system relating to an embodiment of a collection probe.

First, the flow system was set up, including a cell suspension, holder for 6 probes, and a peristaltic pump along a flow system loop, as shown schematically in FIG. 3D. The flow velocity was 1 cm/s in the experiments. In Experiments 1 and 2, the tubing diameter was 2 mm. In experiments 3 and 4, the tubing diameter was 3 mm. The cells were suspended in cell culture medium with FBS and additives. For each run of 30 min, 4 wires were introduced in the flow system at the same time. For all experiments, the wires were tested in a randomized approach, e.g., wires with different windings were mixed in each run.

HUVEC were cultivated to a confluence of 90-100%. They were incubated in 0.5× Trypsin-EDTA for 2 min and removed from the cell culture flask. After washing they were stained with 0.25 µM CFDA for 10 min at 37° C. They were suspended at a concentration of 50,000 cells/ml in 7 (2 mm tubings) or 9 ml (3 mm tubings) cell culture medium.

After incubating the wires in the flow system, the number of cells per wire were counted.

Not to be limited by theory, it was hypothesized that the number of cells or other markers bound to the probe would increase, such as in a linear fashion, with the number of windings. This was postulated to be related to the fluidic properties of the flow system and the shape of the probe.

Figure 3E:
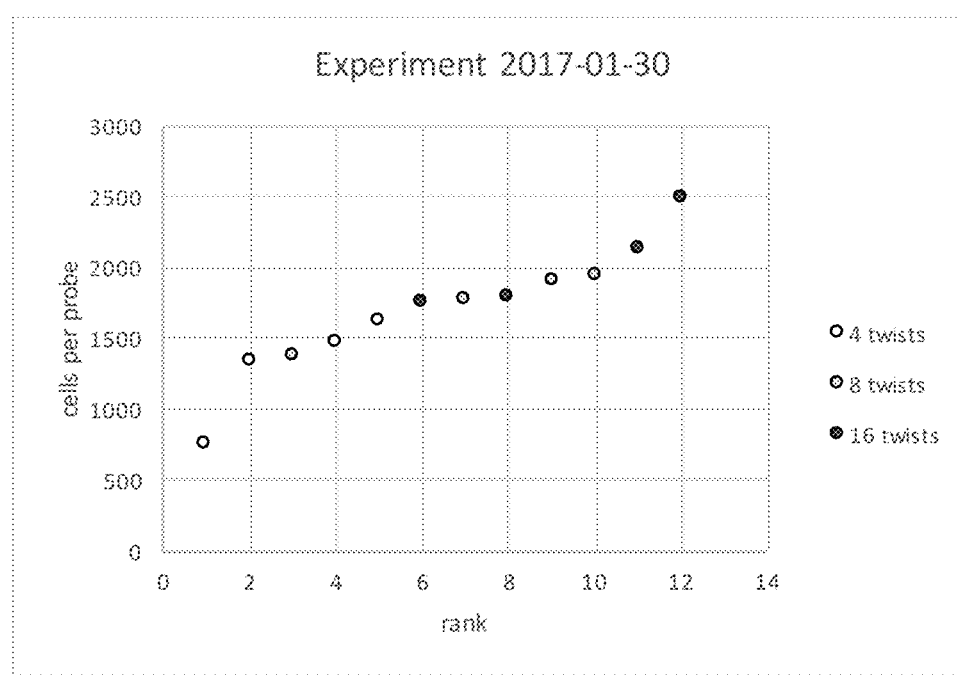
Figure 3F:
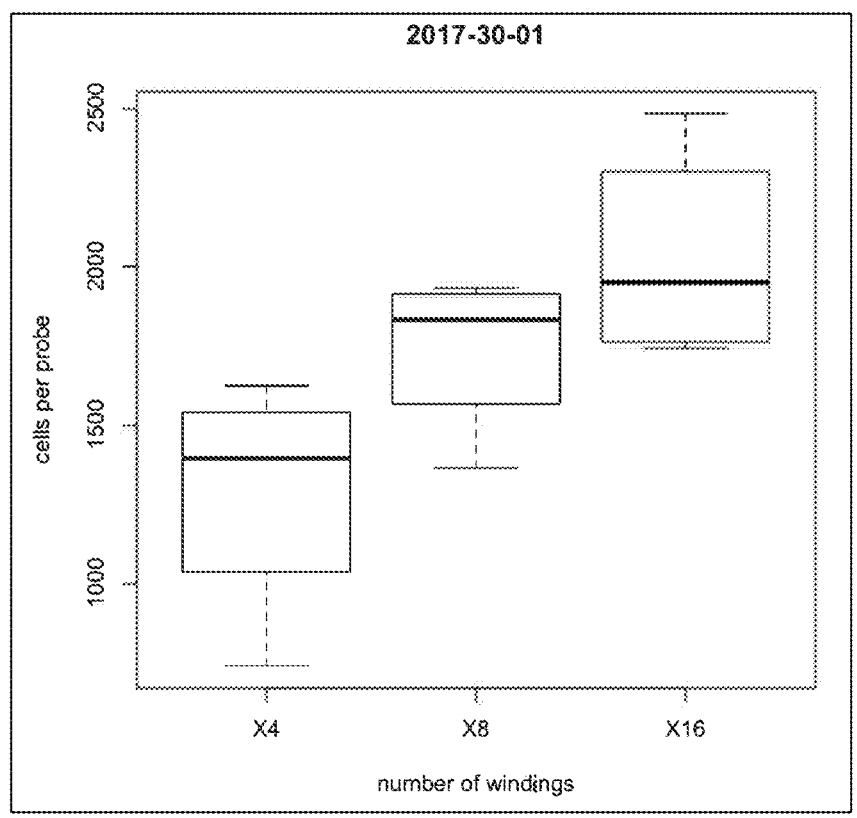
Figure 3G:
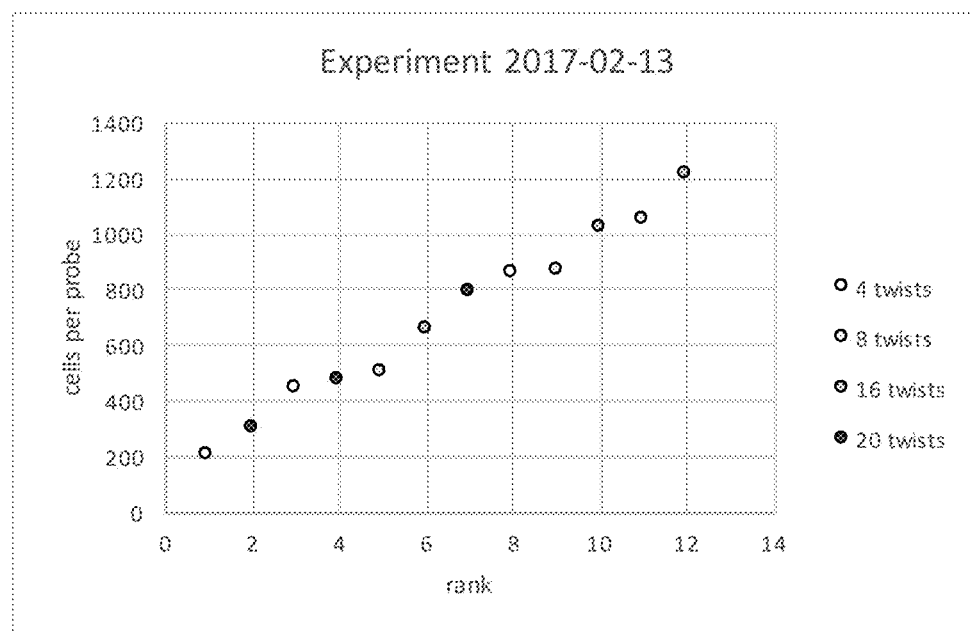
Figure 3H:
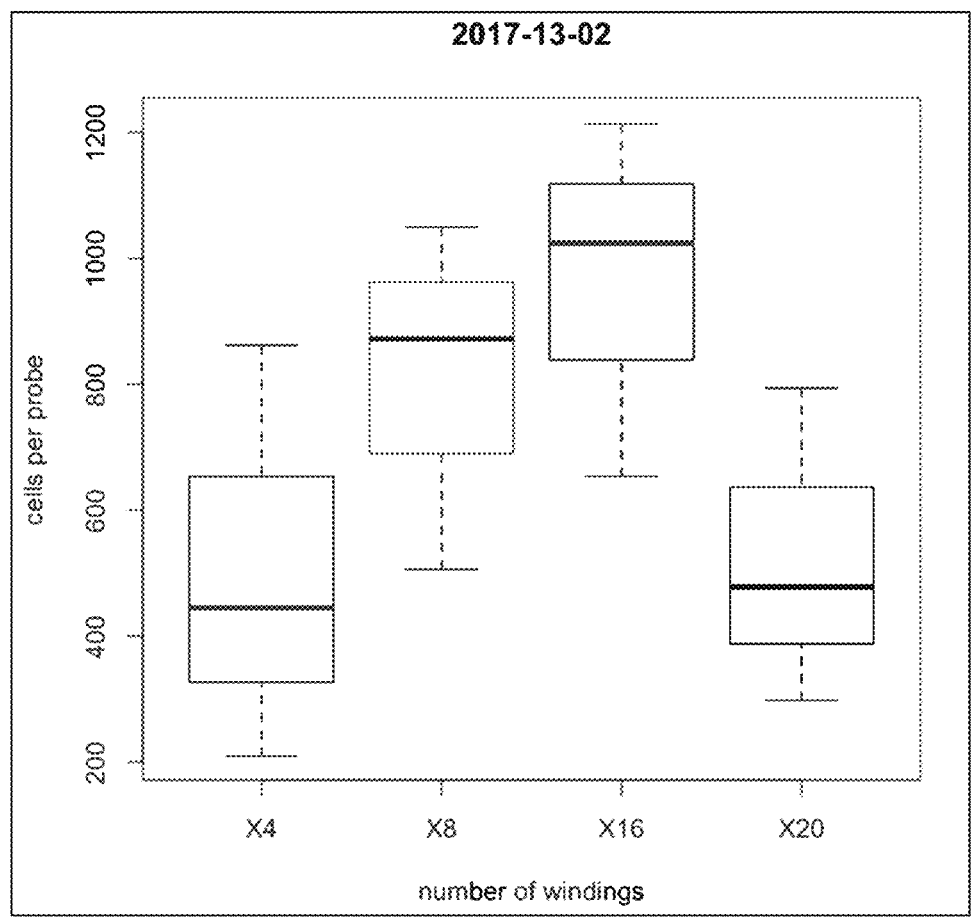

However, unexpectedly and surprisingly in the experiments, probes with 16 windings per 4 cm in length (4 windings per 1 cm in length) showed the highest amount of bound cells, compared to probes with 4 windings per 4 cm in length) (1 winding per 1 cm in length) and 8 windings (2 windings per 1 cm in length) in the same experiment, wires with 20 windings per 4 cm in length (5 windings per 1 cm in length) did not show improved cell binding, and in fact showed decreased cell binding compared to the 16 windings per 4 cm in length. Data from selected experiments are shown in Tables 1 and 2 below, as well as FIGS. 3E-3H. FIG. 3E is a graphical analysis of results of experiment 2 showing rank distribution, while FIG. 3F is a boxplot of the data. FIG. 3G is a graphical analysis of results of experiment 3 showing rank distribution, while FIG. 3H is a boxplot of the data.

TABLE 1

Results of cell counting for experiment 2.

| Cell count | windings |
| --- | --- |
| 740 | 4 |
| 1332 | 4 |
| 1364 | 8 |
| 1456 | 4 |
| 1624 | 4 |
| 1744 | 16 |
| 1768 | 8 |
| 1784 | 16 |
| 1896 | 8 |
| 1932 | 8 |
| 2120 | 16 |
| 2484 | 16 |

TABLE 2

Results of cell counting for experiment 3.

| Cell count | windings |
| --- | --- |
| 211 | 4 |
| 300 | 20 |
| 447 | 4 |
| 480 | 20 |
| 508 | 8 |
| 656 | 16 |
| 796 | 20 |
| 864 | 4 |
| 872 | 8 |
| 1016 | 16 |
| 1052 | 8 |
| 1215 | 16 |

Figure 4:
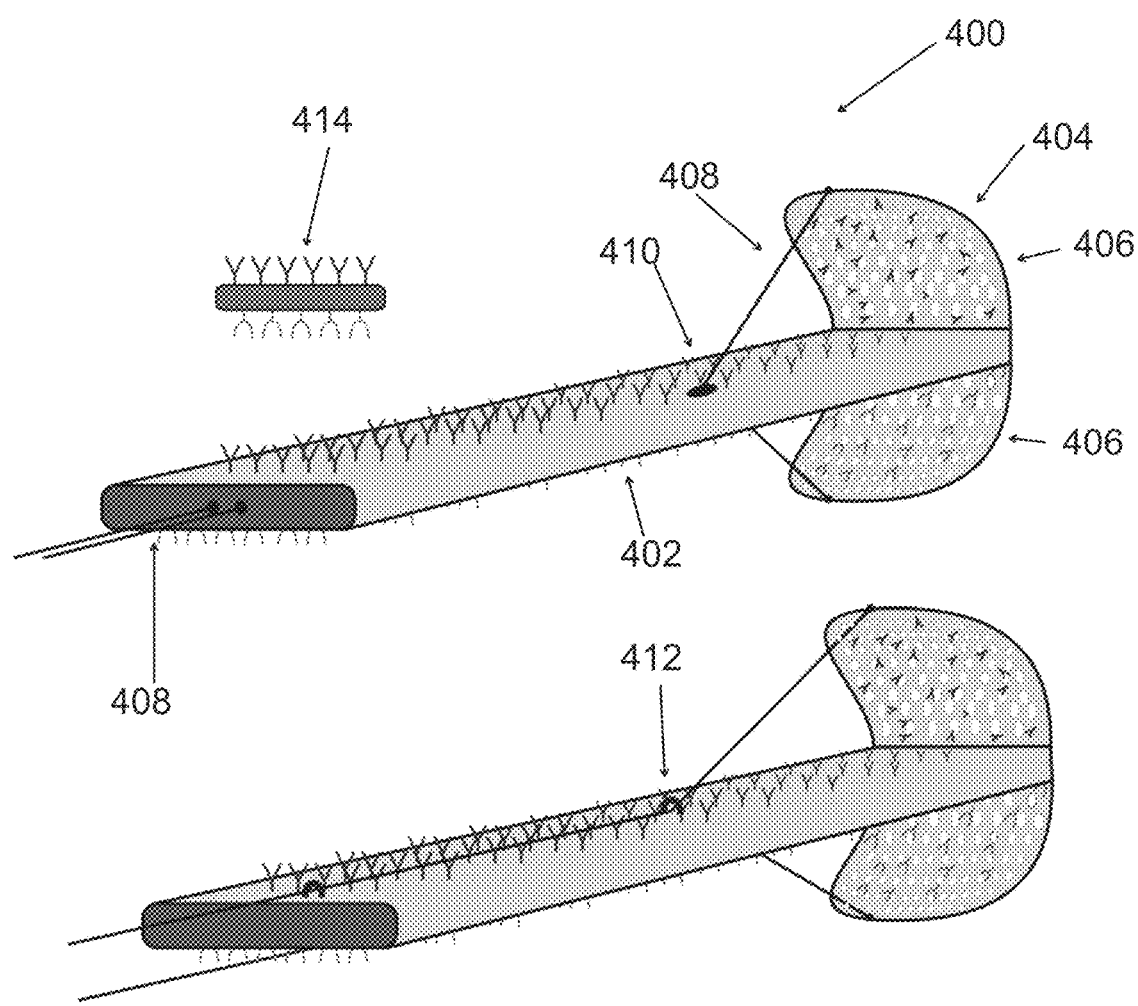
FIG. 4 illustrates another schematic embodiment of a detection device that can include an elongate functional member which can have generally opposing functional surfaces as shown.

FIG. 4 illustrates another schematic embodiment of a detection device 400 that can include an elongate functional member 402 which can have generally opposing functional surfaces as shown. The functional member 402 can have a square, rectangular, or other cross-section as previously described. The distal end of the functional surface can support a sieve 404 with apertures to allow fluid flow therethrough, as well as to bind materials of interest. The sieve 404 can include a plurality of flaps/extensions 406 having apertures therethrough, such as 2, 3, or 4 extensions, and having longitudinal axes that are substantially orthogonal or at other angles to the functional member 402. In some embodiments, the surfaces of the sieve 404 can also serve as functional surfaces. In some embodiments, the flaps 406 can be regularly or irregularly spaced apart, such as spaced apart by 60, 90, 120, or 180 degrees in some cases. In some embodiments, the distal ends of the flaps 406 can be operably connected to one or more tension members 408, which can allow the flaps 406 to radially open, or fold back/close such as proximally back toward the functional member 402 and close to allow for a decreased crossing profile advantageous for removal of the device 400. The tension members 408 can run through apertures 410 (as shown in the upper figure), eyelets 412 (as shown in the lower figure), channels, or other elements axially along the functional surface, through the functional member, or otherwise for enhanced control in some cases. The functional member can include one, two, or more binding members, such as a bifunctionally charged functional member as illustrated schematically 414.

Figure 5:
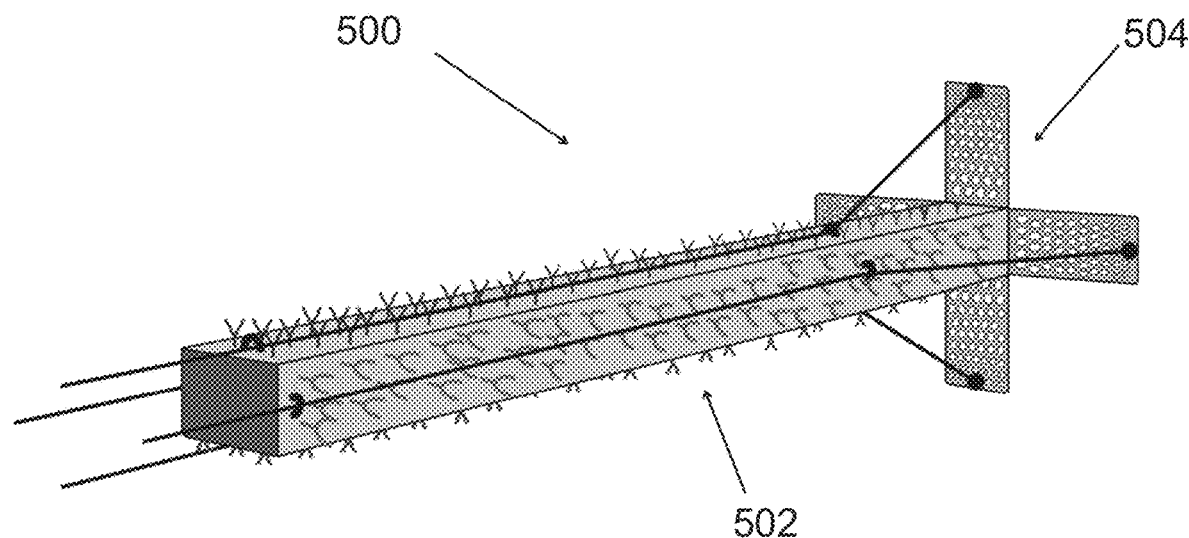
FIG. 5 illustrates an embodiment of a detection device similar to that of FIG. 4, FIG. 6 schematically illustrates a detection device with blood flowing inside a lumen of, as well as outside of a functional member having a generally cylindrical cross-section.

FIG. 5 illustrates an embodiment of a detection device 500 similar to that of FIG. 4, with an elongate functional member 502 having a width that can be at least about 1.5×, 2×, 2.5×, 3×, 3.5×, 4×, 5×, 6×, 7×, 8×, 9×, 10×, or more with respect to the thickness of the elongate functional member. The distal end of the elongate functional member can be operably attached to a plurality of flaps as previously described, which can move radially outwardly or inwardly via tension members operably connected proximally to a control actuated by an operator. The flaps 504 can form various shapes depending on the desired clinical result, such as a cross as shown.

Figure 6:
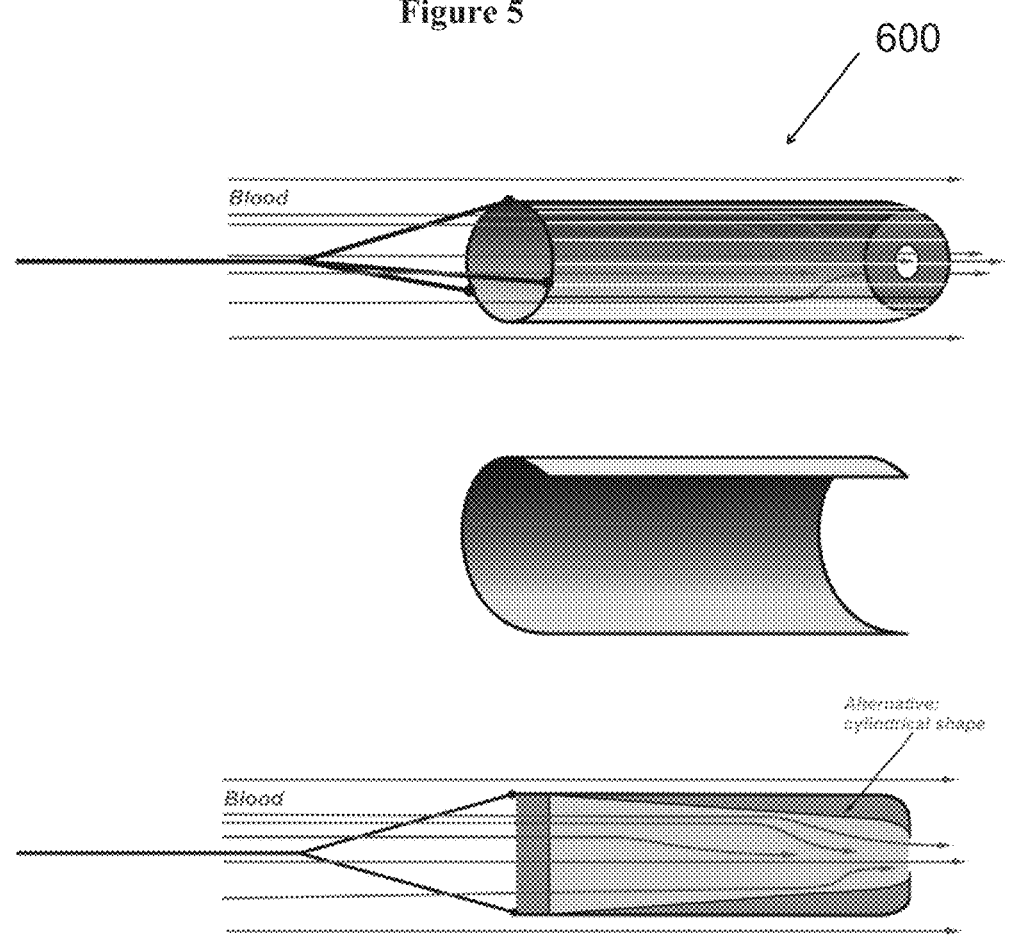

FIG. 6 schematically illustrates a detection device 600 with blood flowing inside a lumen of, as well as outside of a functional member having a generally cylindrical cross-section. The sidewall of the lumen can be frustoconical or another geometry, having a first wider diameter proximally gradually or stepwise narrowing to a second narrower diameter distally as illustrated in the lower figure.

Figure 7:
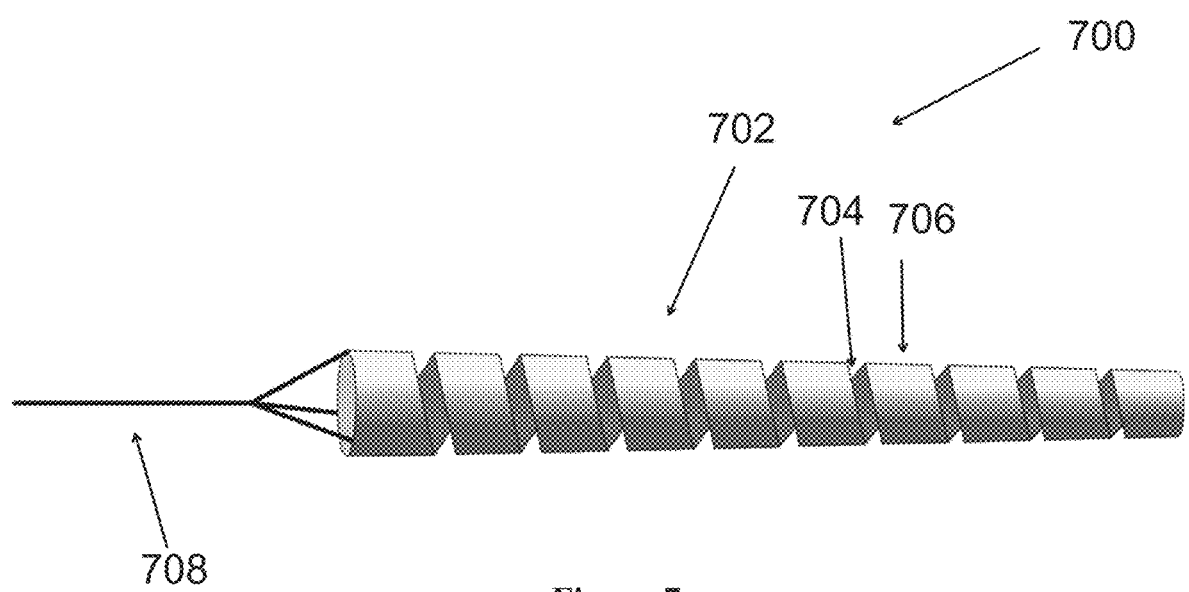
FIG. 7 schematically illustrates a coiled functional member as part of a detection device with slots or other spaces in between revolutions of the coils, attached proximally to a tether line.
Figure 8:
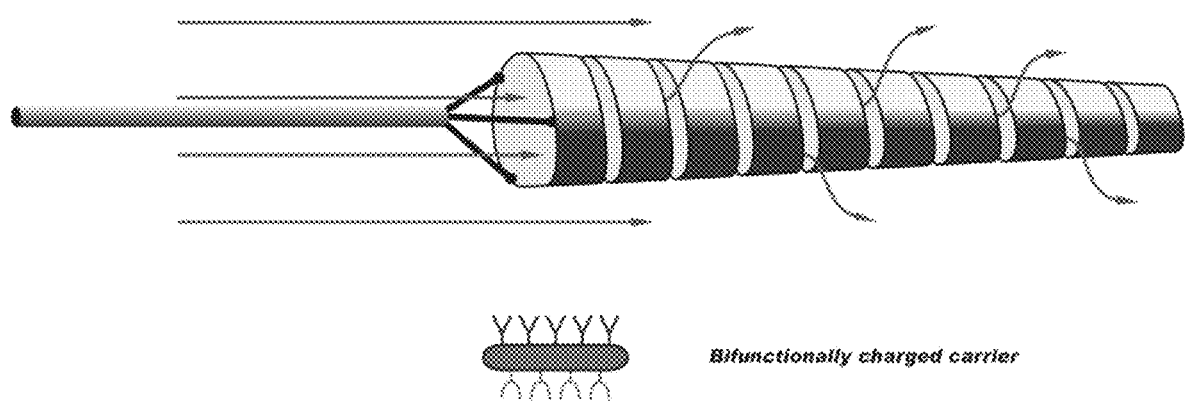
FIG. 8 illustrates schematically the embodiment of FIG. 7, wherein blood can flow inside the lumen of, outside of, and through the slots and spaces in between revolutions of the coils.

FIG. 7 schematically illustrates a coiled functional member 702 as part of a detection device 700 with slots 704 or other spaces in between revolutions 706 of the coils, attached proximally to a tether line 708. As previously described, the coiled functional member 702 can include a shape memory material allowing it to curl/twist/roll within the body lumen (e.g., via exposure to body temperature, induction, or other forms of heating) and uncurl/untwist/roll when removed from the body. In some embodiment, removal of the detection device can involve cooling the functional member to allow for the transformation to a relatively straightened configuration (e.g., via injection of media such as cold saline into the target blood vessel, conduction cooling, etc.). FIG. 8 illustrates schematically the embodiment of FIG. 7, wherein blood can flow inside the lumen of, outside of, and through the slots and spaces in between revolutions of the coils. The functional surface can include a bifunctionally charged carrier in some cases as previously described herein.

In some embodiments, the detection or collection device can include an atraumatic distal tip, in order to avoid cutting or puncturing the body lumen, such as a blood vessel including an artery or vein for example. In some embodiments, the atraumatic tip can be a rounded and/or blunt tip. This can be achieved in some cases by cutting wires with a blade, laser, or the like to provide a desired shape, such as rounded in some cases, and, in another step, removing the sharp edge of the wire by selective etching in acid. Cutting can be, for example, a fully automatic process running with high efficiency. The etching step can be performed manually or automated as well. The tip (for example, about or up to about 3 to about 4 mm in some cases) of each wire can be placed for a desired period of time, such as a few seconds in concentrated acid (e.g., sulfuric or nitric acid). After etching the tips of the wires, the wires can then be washed in a solution such as ultra clean water in order to stop the process and remove acid residues from the surface.

Some embodiments of devices disclosed above can be used in a method including one or more of the following. A guide element or wire that includes a functional surface can be used to insert the structure into an anatomical structure such as human body lumen or solid tissue, such as, for example, an artery, vein, lymphatic, or other body lumen via, for example, a percutaneous route or a cut-down procedure, or within the lumen of an input port such as an intravenous catheter placed prior to or concurrent with the probe. The probe can be fully inserted into the desired body lumen, or partially inserted with the functional surface fully within the target region of interest of the body in some cases, while a proximal non-functional region of the probe may remain outside of the body. The wire can include in some embodiments a proximal handle or hub that can remain outside of the body while the probe is inserted into the body lumen for a desired period of time, such as about, at least about, or no more than about 1, 2, 3, 4, 5, 6, 7, 8, 9, 10, 15, 20, 25, 30, 35, 40, 45, 50, 55, 60, 120, 180, 240, 360, or more minutes. The probe can be maintained in a fixed position for the desired period of time, or moved in some embodiments. The probe can then be removed from the body lumen in some embodiments. In some embodiments, the probe is detached from a proximal handle and partially or fully maintained within the body lumen for a period of time, and then retrieved with a separate retrieval tool later.

In some embodiments, as one non-limiting example, prior to use of the probe, an 18 gauge is inserted into the basilica vein, cephalic vein, or medial cubital vein, all located in the antecubital fossa in the arm. The stylet is removed from the peripheral venous IV and discarded. A cap of the probe is removed and a connector of the probe is screwed or otherwise removably attached to the IV. The probe is carefully inserted into the vein through the IV until a second mark location/location is reached. In this position, the functional area of the probe will be in the vein. The probe can be removed after, for example, 30-60 minutes through the IV, after that IV can be removed. The probe can then be processed and sent for analysis.

Although the probe can be described in some cases in terms of an insert to be temporarily placed down an existing access port or sheath into the cardiovascular system, for retrieving a marker from blood, broader applicability is also possible in some embodiments. Existing access ports or sheaths include but are not limited to Hickman catheters, Portacath catheters, peripherally inserted central catheter (PICC) lines, femoral, jugular, or subclavian central venous lines, radial arterial catheters and peripheral venous lines. Furthermore, additional procedures, such as transseptal puncture and transjugular intrahepatic puncture, may be used to access other body sites such as the arterial chambers of the heart or the portal vein, respectively. For example, the probe may be adapted for direct access to a target site, without the use of a distinct tubular access catheter, in general, whether used with an access sheath or as a stand alone device, the dimensions of the probe can be optimized by persons of skill in the art in view of the present disclosure to suit any of a wide variety of target sites. For example, a probe can be used to obtain samples from large and small arteries and veins throughout the cardiovascular system, as well as other lumens, potential spaces, hollow organs and surgically created pathways. Marker (tumor and/or non-tumor) collection may be accomplished in blood vessels, body lumens or cavities, such as the lymphatic system, esophagus, trachea, urethra, ureters, fallopian tubes, intestines, colon, biliary ducts, spinal canal and any other locations accessible by a flexible or rigid probe which may contain a specific binding partner of diagnostic value. The probe may also be adapted in some cases for direct advance through solid tissue, such as soft tissue or through bone, for site specific monitoring of a binding partner or binding partners of interest.

In some embodiments, the guide element may include, or be coated by a layer of one, two, or more of a metal, polymer, glass or a combination of materials. The metal could be, for example, Nitinol, Elgiloy, stainless steel, platinum, platinum/iridium, tungsten, gold, silver, or another material. In some embodiments, the diameter of the guide element or wire is in the range of 0.1 mm to 1 mm and the overall length of the guide wire is 100 mm to 200 mm. In some embodiments, the wire can have sufficient column strength to be advanced to a desired target site without undesirable bending or kinking.

In some embodiments, the conical and/or linear functional surface, if present, may be soldered (if it is composed of metal) or molded (if it is composed of polymer) to the guide element or wire. In some embodiments, the conical structure is directly formed from the guide element or wire.

The terms "binding partner," "binding agent" or "member of a binding pair" refer to molecules that specifically bind other molecules (e.g., a marker of interest) to form a binding complex such as antibody-antigen, lectin-carbohydrate, nucleic acid-nucleic acid, biotin-avidin, etc. In certain embodiments, the binding is predominantly mediated by covalent or noncovalent (e.g. ionic, hydrophobic, etc.) interactions. One or more binding partners that specifically bind a target marker to be detected can be affixed in the binding zone on the probe of the invention. The binding partner(s) can be selected based upon the target marker(s) that are to be identified/quantified. Thus, for example, where the target marker is a nucleic acid the binding partner is preferably a nucleic acid or a nucleic acid binding protein. Where the target marker is a protein, the binding partner is preferably a receptor, a ligand, or an antibody that specifically binds that protein. Where the target marker is a sugar or glycoprotein, the binding partner is preferably a lectin, and so forth. A device of the invention can include several different types of binding partners, for example, multiple nucleic acids of different sequence and/or nucleic acids combined with proteins in the same device. The latter would facilitate, e.g., simultaneous monitoring of gene expression at the mRNA and protein levels. Other combinations of different types of binding partners can be envisioned by those of skill in the art and are within the scope of the invention. Furthermore, the binding partner may be combined with an optically sensitive dye to facilitate assessment of bound CMCs.

In some embodiments, the functional surface solves the problem of requiring antibodies as binding agents by using small engineered fusion proteins for capturing cells from body fluids which include non-immunoglobulin binding molecules with specificity for markers on these cells, linkers, an attachment site to a solid support, and a protease cleavage site for gentle cell release from the support and which do not comprise an IgG-Fc part prone to undesired cell interactions.

In some embodiments, a detection device can be configured to detect rare cardiovascular cells (heart, kidney or cerebral) in vivo, which may have a detection area coated with fusion proteins for isolating and/or capturing biological receptor molecules.

In some embodiments, the detection area may include areas that include the structure B-L1-PCS-L2-C, C-L2-PCS-L1-B, B-PCS-L1-C, or B-L1-PCS-C and may be coupled to a guide wire, wherein B is a non-IgG-binding molecule that is capable of binding a diagnostically relevant target wherein the binding of the target enables the isolation and or capturing of cells expressing the target on their surface or of the molecule from body fluid; L1 is a first peptide linker for enabling access of the protease to the protease cleavage site; PCS is a protease cleavage site wherein the specific cleavage of the PCS eliminates the covalent bond between the coupling moiety C and the specific binding protein B and releases the captured cells or soluble molecules from the solid support; L2 is a second peptide linker for enabling access of the protease to the protease cleavage site; and C is a moiety for chemical coupling to an attachment site on a solid support.

In some embodiments, the guidewire may include a metal, or a polymer.

In some embodiments, the overall length of the guide wire and the functionalized structure is between about 100 mm to about 300 mm.

In some embodiments, the diameter of the functionalized structure is between about 0.3 mm to about 3 mm.

In some embodiments, the functional area of the probe/guidewire after the collection process can be split (e.g., cut) into a plurality of segments such as 2, 3, 4, or more segments such that the pieces can be subject to different analyses. For example, in some embodiments, one piece can be utilized for genomic analysis with another piece can be utilized for immunostaining. In some embodiments, the functional area can include features to facilitate subdivision/splitting/detachment, such as a cut-away, tear-away, perforation line, or other type of mechanical or other detachment (e.g., electrolytic detachment).

In some embodiments, indicia of a desired geometry, such as squares for example can be printed onto the functional (e.g., flat) surface(s) of the probe to allow for expedited automatized image-based or other analyses, e.g., of cells or other material.

In some embodiments, with the assistance of a fluid (e.g., urine) flow system, it can be possible to bind a material of interest, e.g., cfNA on a probe under defined flow conditions. One non-limiting example setup is designed for 7 probes with 18 mL or more of urine. It is possible to reduce or to expand the flow system depending on the desired clinical result.

Figure 9A:
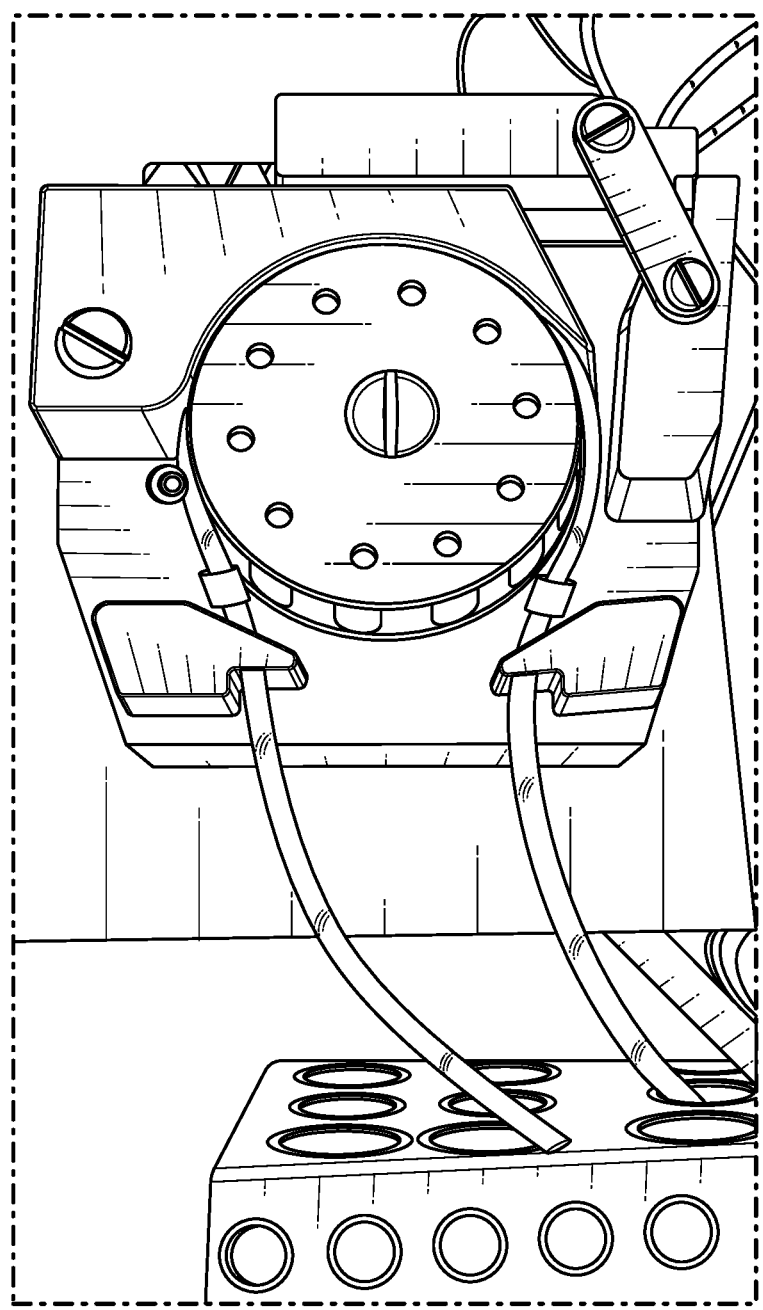
FIGS. 9A-9R illustrate various components of a flow system that can include one or more probes therethrough for in vitro collection of a patient specimen.
Figure 9B:
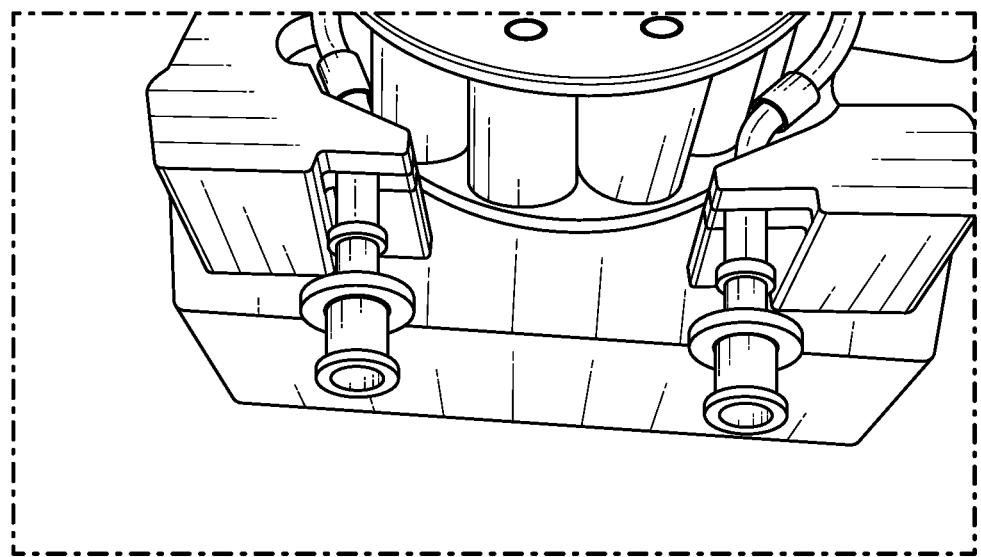

Set up of an example Flow System for probes can include any number of the following:

Use racks for increasing the height of the system to avoid undesired bending of the silicone tube and to facilitate a stable base;

Insert stopper hose in head of pump as illustrated in FIG. 9A;

Connect on both ends of stopper hose the Luer tubing connector as shown in FIG. 9B;

Prepare silicone tubes—following lengths can be used as non-limiting examples: 1×25 cm; 1×15 cm; 6×6 cm; 1×20 cm;

Prolong/extend the stopper hose with silicon tubes; (Input side (right): 25 cm; Output side (left): 15 cm)

Figure 9C:
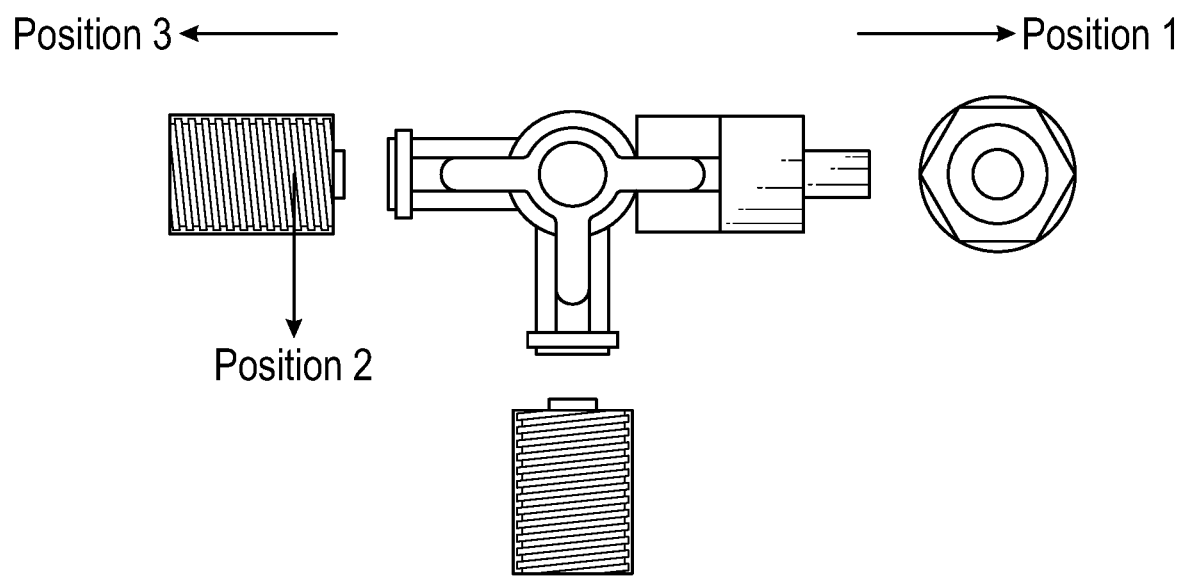
Figure 9D:
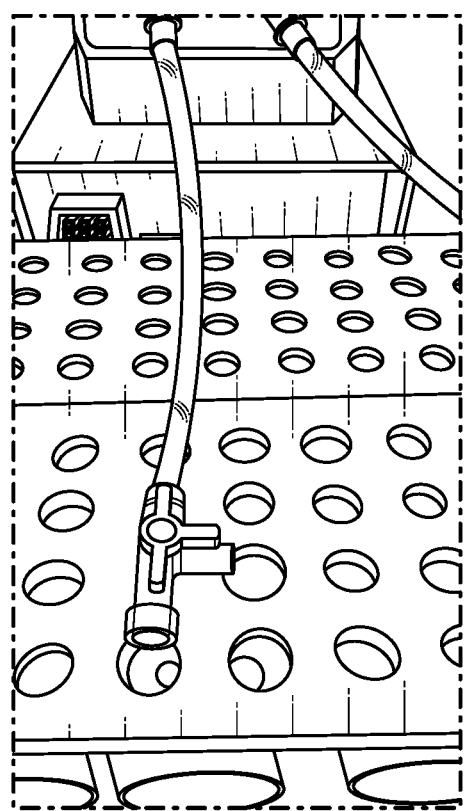
Figure 9E:
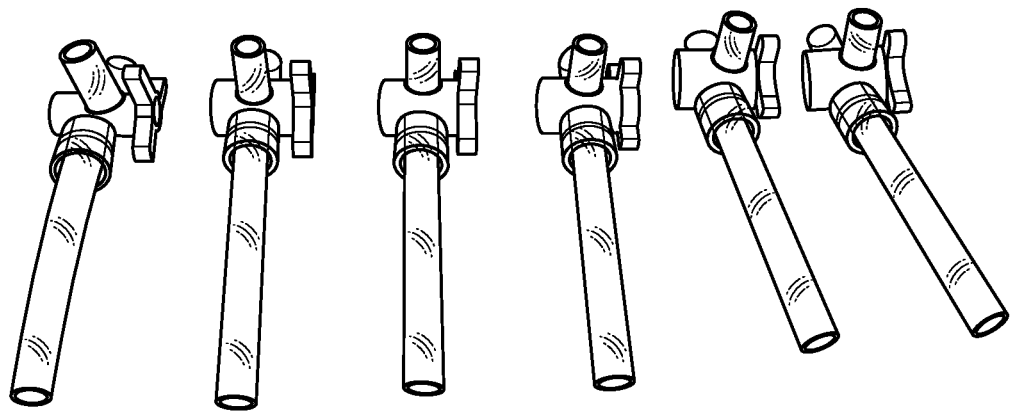
Figure 9F:
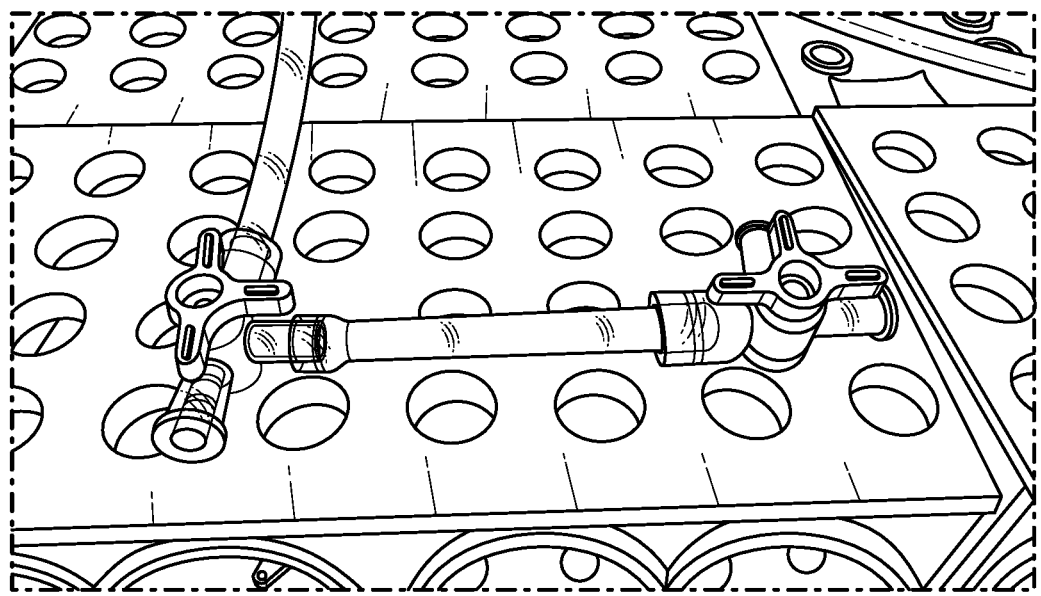
Figure 9G:
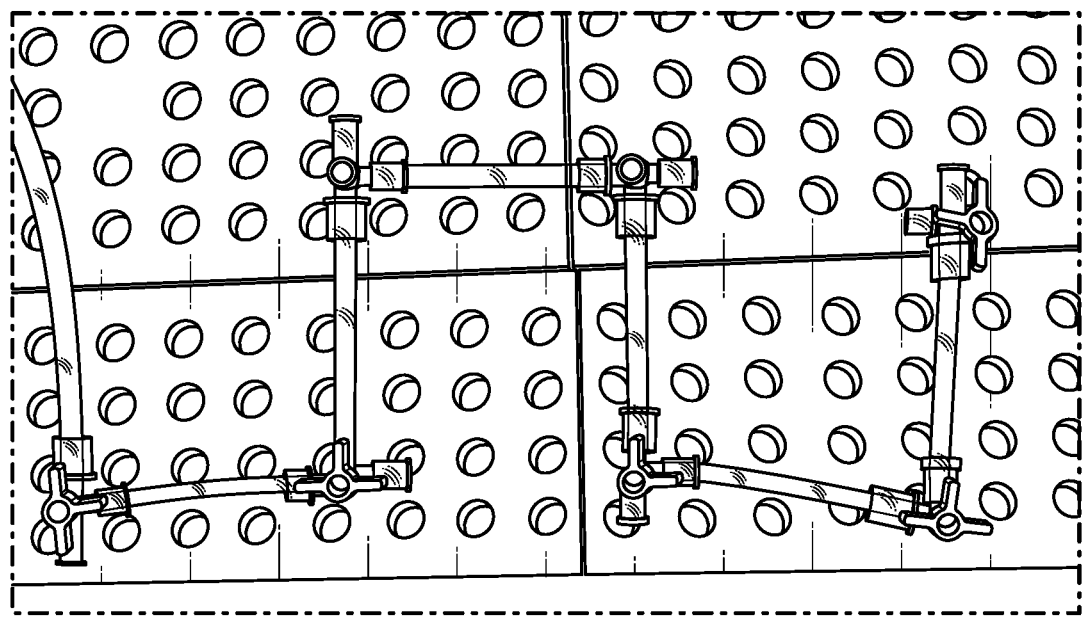
Figure 9H:
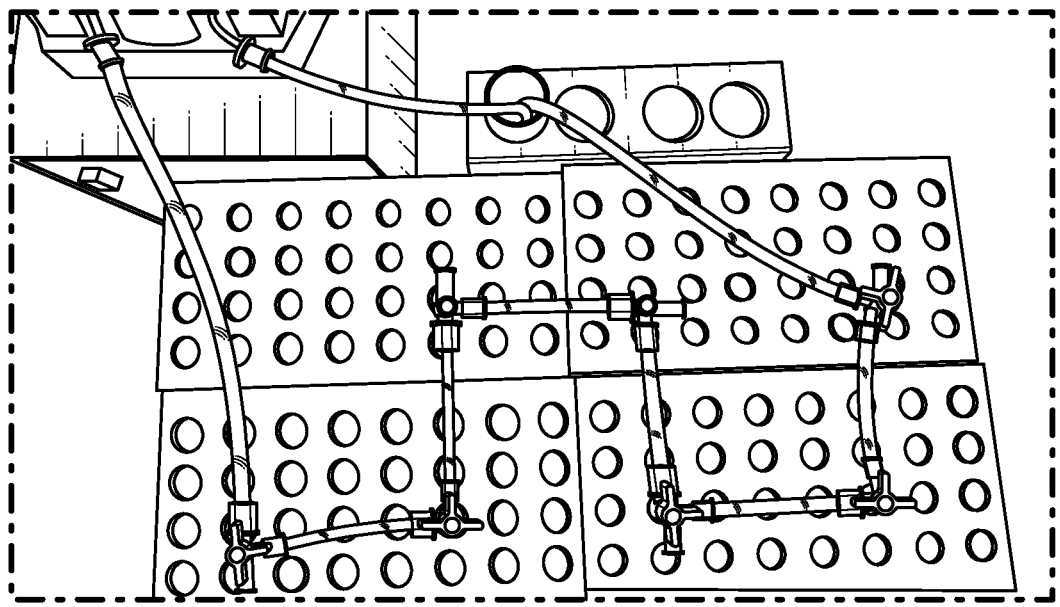
Figure 9I:
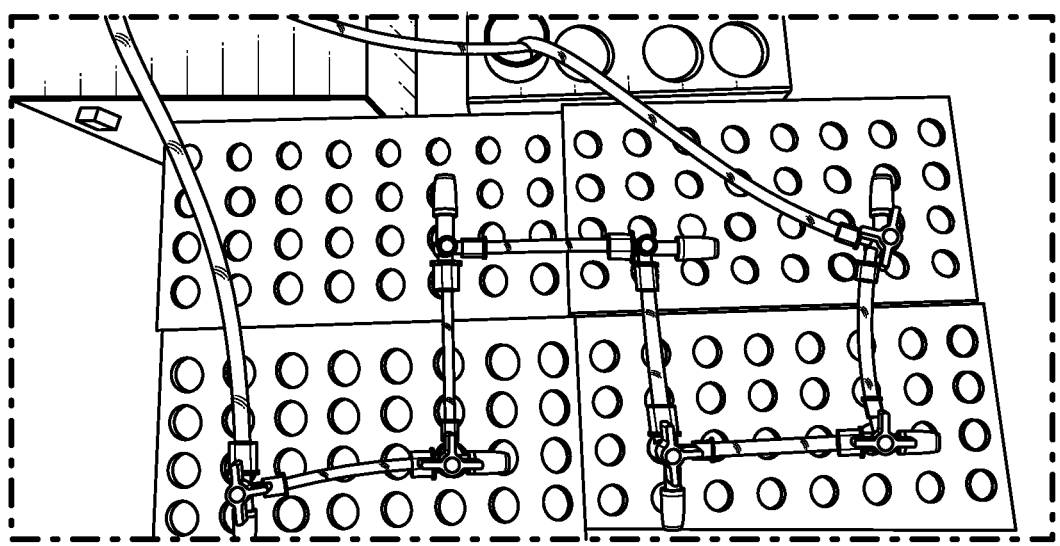

The long end can be used to aspirate cell suspension from 50 mL test tube, such as, e.g., a FALCON Conical Centrifuge Tube (Thermo Fisher Scientific, Waltham, Mass.)—put this end in the 50 mL FALCON;

The short silicone tube can be used in connection with a 3-way-valve, as illustrated in FIG. 9C having 3 positions; a first Position 1; a second Position 2 at a right angle to Position 1; and a third Position 3 at a right angle to Position 2 and spaced about 180 degrees apart from Position 1. Position 1 can be used on the 3-way valve to fix the silicon tube, as shown in FIG. 9D. Additional 3-way valves can then be prepared. Each 6 cm silicone tube can be used and connected to 3-way valves at Position 1, as shown in FIG. 9E. An assembly can be taken and 3-way valve(s) can be plugged in at Position 2, as shown in FIG. 9F. This can be repeated for the other assemblies, as shown in FIG. 9G. For the last 3-way valve, a silicone tube (e.g., about 20 cm in length) can be used to connected to the 50 mL FALCON tube, as shown in FIG. 9H. All 3-way valves can then be closed with injection stoppers, as shown in FIG. 9I, to form a closed loop.

The system can then be blocked to avoid non-specific binding interactions, such as for Western Blot, ELISA, IHC, and/or nucleic acid detection methods. A blocking agent can saturate excess protein-binding sites on membranes and microplates in immunoassays to reduce background interference. For example, 20 ml of 3% BSA/PBS (phosphate-buffered saline) can be placed in a 50 mL tube. The pump can be activated with the appropriate velocity. Once the whole system is filled with the blocking agent, the pump can be stopped and incubation can occur at room temperature for an appropriate period of time, such as about 30 minutes in some cases. The system can be checked for the absence of bubbles. Bubbles present can be manually flicked on the tube to move the bubble to the end of the tube. After blocking, the flow system can be emptied. The pump can be activated, but remove aspirate silicone tube from the 50 mL test tube so no further BSA will be aspirated, just air so the system will be soon emptied.

Figure 9J:
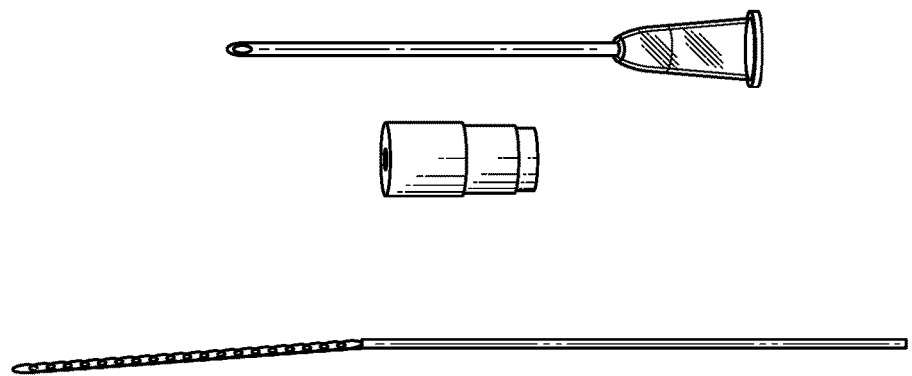
Figure 9K:
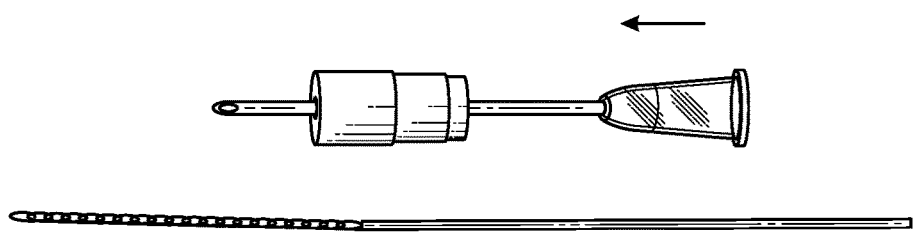
Figure 9L:
Figure 9M:
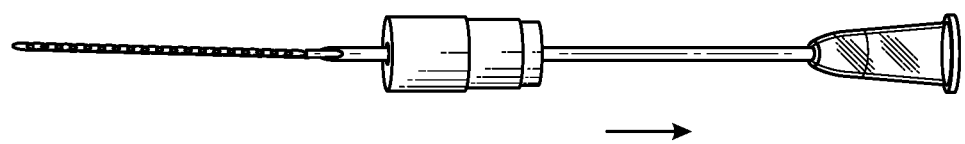
Figure 9N:
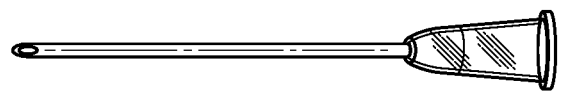
Figure 9N:
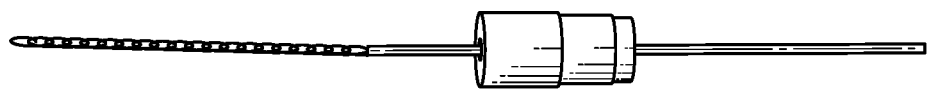

The system can then be refilled with the sample to be tested, such as a urine sample in some embodiments. FIG. 9J illustrates an embodiment that includes a needle/cannula, stopper including a septum, and probe. In some embodiments, the probes preferably include the stopper (e.g., yellow stopper) in order to close the flow system. The needle can then be pushed through the injection stopper in an appropriate direction indicated by the arrow, such as from the top to the bottom, as illustrated in FIG. 9K. As illustrated in FIG. 9L, the probe can be gently slid through the cannula in an opposite direction (e.g., bottom to top) as indicated by the arrows, until an appropriate distance is reached, e.g., about 2 cm in some cases, before an end of the functional area of the probe, as indicated in FIG. 9M. Care is preferably taken to avoid touching or scratching the functional area of the probe with the cannula. Next, the cannula is gently removed in the appropriate direction (e.g., bottom to top) through the septum of the injection stopper.

Figure 9O:
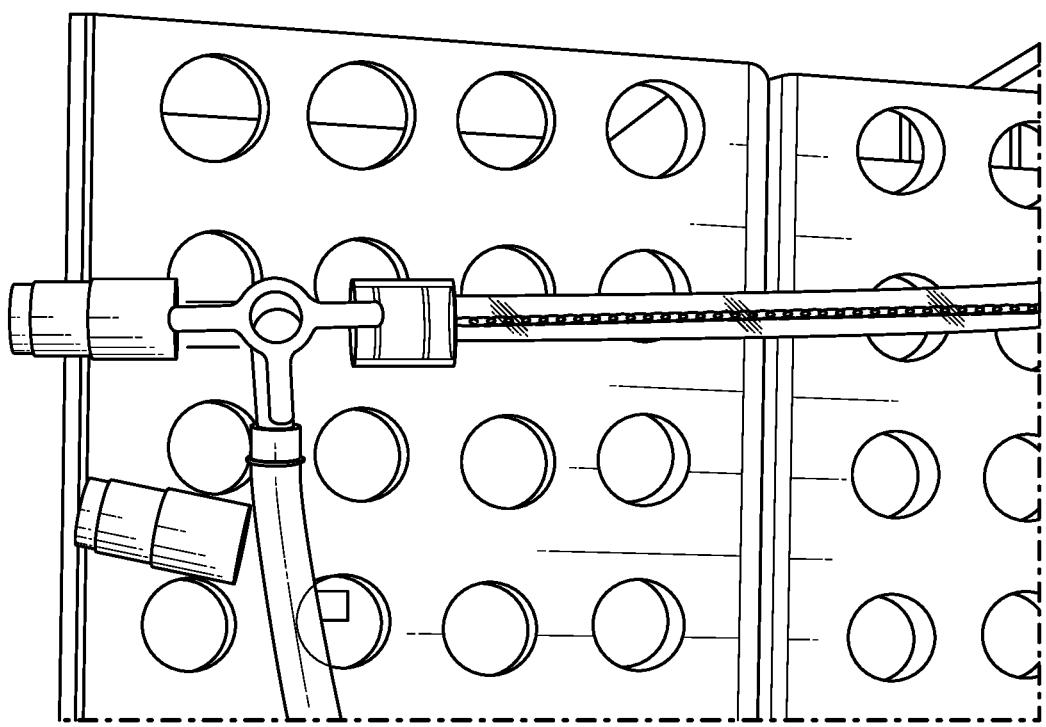
Figure 9P:
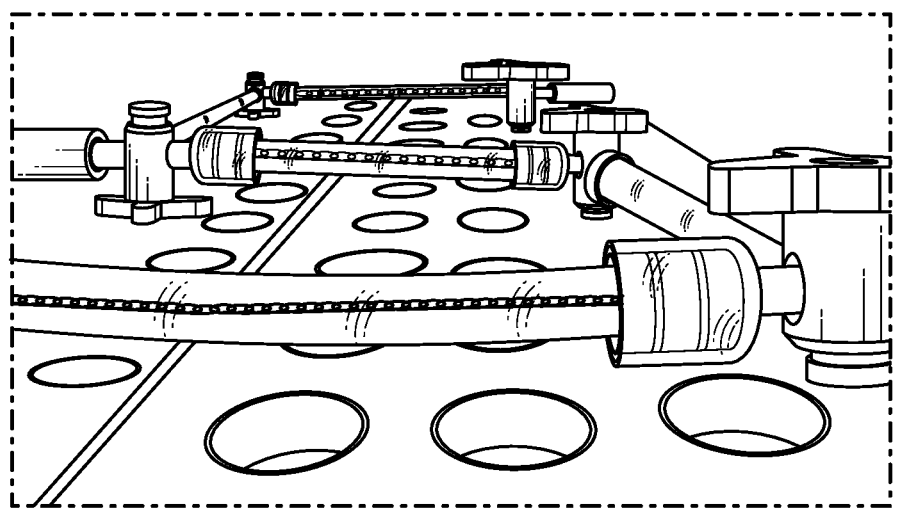
Figure 9Q:
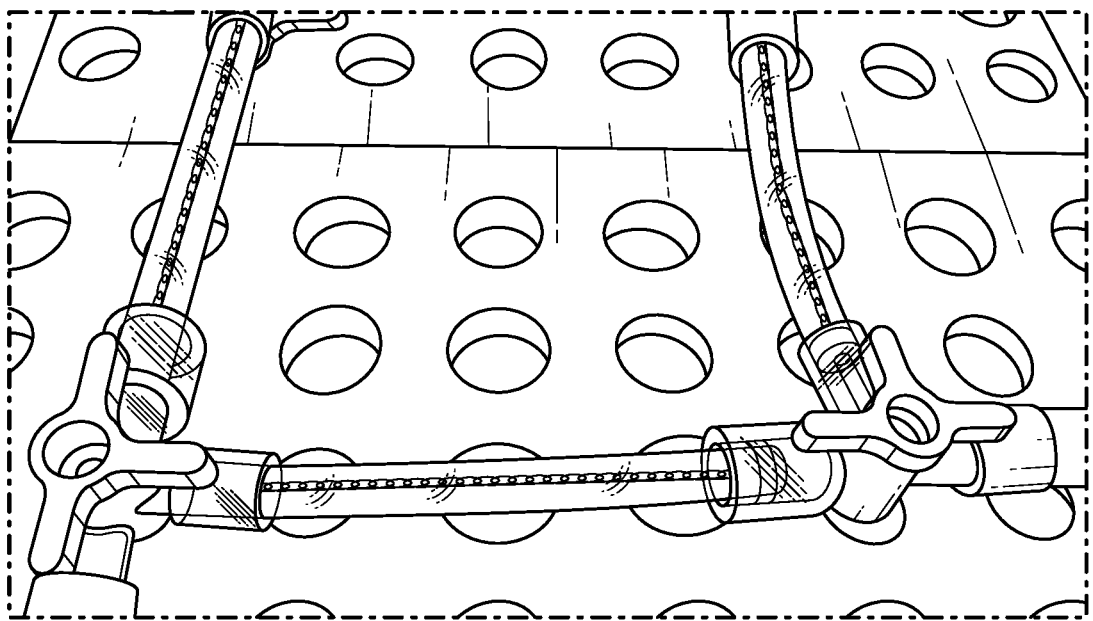
Figure 9R:
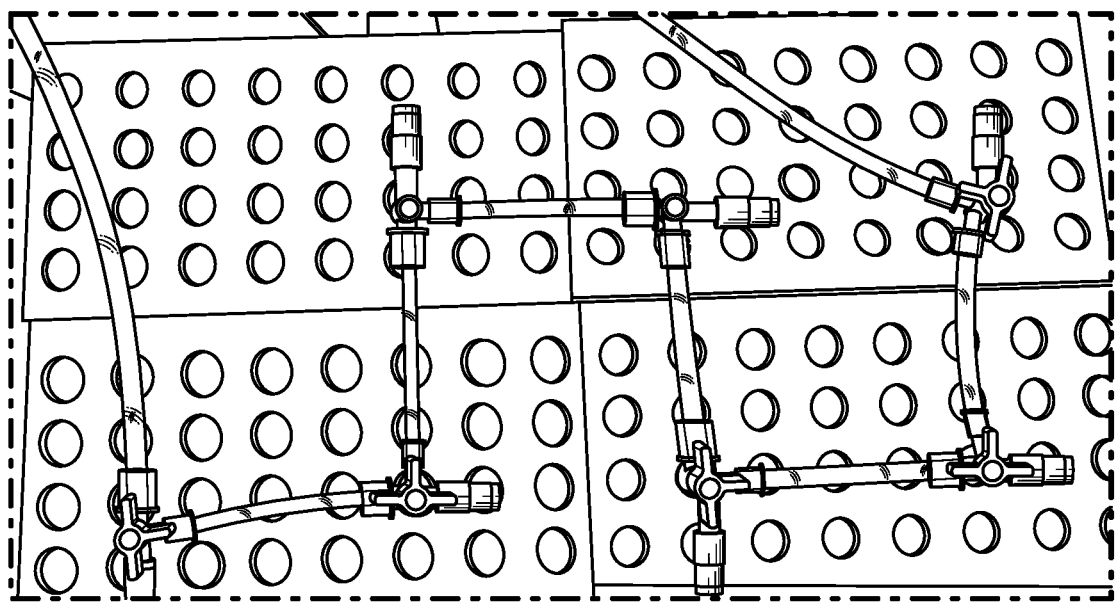

The first 3-way valve can then be opened by removing the injection stopper, as shown in FIG. 9O. The probe can then be carefully inserted without touching the indwelling surface/inside diameter of the 3-way valve or silicon tube, as shown in FIG. 9P. This can be repeated for each of the remaining probes, as shown in FIGS. 9R-9S. The functional part of the probe can be in some cases positioned in the middle of the silicone tube (e.g., 6 cm silicone tube). The application time can start when all of the probes are inserted in the system, The system can then be incubated for an appropriate period of time, such as about or at least about 30, 45, 60, 75, 90, 120, or more minutes.

The probes can be removed in the same direction as the insertion direction, taking care to avoid contact with the inside diameter/wall of the 3-way valve or silicone tubing to avoid scratching. The probe can then be placed in an appropriate container such as a wash glass, and the 3-way valve closed with its original lid. This process can be repeated for each probe. Each probe can be placed in its own wash glass. Each probe can then be washed an appropriate number of time, such as twice in some cases, in a solution, such as gently dipping the probe in 1×PBS in some embodiments.

In some embodiments, the fusion proteins may include one, two, or more specific IgG or non-IgG binding molecule with specific binding affinity to a target molecule of interest; and/or binding to a diagnostically and/or therapeutically relevant target that may include a tumor cell surface target or soluble molecule such as, for example, EGFR, EpCam, Her2, MUC1, CD146, CD133, CD31, CD34, CD105, B7H1/2/H3/H4, gangliosides, HMW-MAA, PDL-1, PDGFR, IGFR, TGFR, MET, HER2/3, interleukin receptors, adhesion molecules, Ig variable chains, TCR or VEGFR1/VEGFR2; and/or binding affinity to non IgG binding proteins such as ubiquitin, mutein (Affilin), scFv, Darpin, Anticalin, or Fynomer.

In some embodiments, the fusion proteins may include a first peptide linker that is not cleavable by proteases present in body fluids, is non-immunogenic, and is, for example, 5-50 amino acids (e.g., 10-30 amino acids) that may be selected from, for example, G, S, A, and/or P.

In some embodiments, the fusion proteins may include a protease cleavage site for a protease which is not present or not effective on the described construct of this invention in the body fluid from which the cells are captured, which may include blood, urine, saliva, and/or cerebral spinal fluid.

In some embodiments, the fusion proteins may include a viral protease cleavage site such as TEV protease cleavage site.

In some embodiments, the fusion proteins may include a second peptide linker that may be identical or different from peptide linker 1, is not cleavable by proteases present in the body fluid, is non-immunogenic, and has 5-50 amino acids (e.g., 10-30 amino acids) that may be selected from G, S, A, and P.

In some embodiments, the fusion proteins may include a coupling moiety, which may have a reactive chemical group that forms covalent bonds with chemical groups of the solid support such as an electrophilic group, a nucleophile group, a redox-active group, a group enabling addition reaction or cyclic addition reaction, Cysteine, NHS, Azide, or Maleimide.

In some embodiments, the guide element may be at least partially designed as a wire, may be at least partially resilient, and may be at least partially designed as a flexible medical guide wire.

In some embodiments, the guide element may be at least partially designed as a thread and may be at least partially a flexible plastic thread, or a catheter.

In some embodiments, the guide element may have a receiving portion for receiving at least one functional element. In some embodiments, the guide element may have a distal end and a proximal end, and in between the distal and proximal ends, the guide element may have a receiving portion adapted to receive at least one functional element. In some embodiments, the probe can include a body having a length dependent upon the desired access site and the desired placement site for the distal end. For example, lengths in the area of from about 1 cm to about 30 cm, between about 1 cm to about 20 cm, between 2 cm and about 20 cm, between 2 cm and about 10 cm, or between 5 cm and about 20 cm can be useful in applications that require the catheter to be advanced down a relatively short tubular access sheath. Longer lengths may be used as desired, such as on the order of from about or at least about 120 cm to about 140 cm for use in percutaneous access at the femoral artery for placement of the distal end in the vicinity of the coronary artery. Intracranial applications may call for a different catheter shaft length depending upon the vascular access site, as will be apparent to those of skill in the art.

In some embodiments, the guide element is formed at least partially helical.

In some embodiments, the guide element has at its outer periphery at least in part an external thread.

In some embodiments, the guide element has a distal end and a proximal end, said distal end being insertable into a blood vessel or body cavity.

In some embodiments, the guide element has a distal end and a proximal end, wherein the distal end is thickened.

In some embodiments, the guide element has a distal end and a proximal end, wherein the proximal end is connected to a stabilizing element.

In some embodiments, the guide element is screwed into an internal thread of the stabilizing element.

In some embodiments, the guide element is manufactured from a metallic and/or non-metallic material.

In some embodiments, the guide element has at its distal portion a functional detection area equipped with receptors.

In some embodiments, the guide element is connected with a stabilizing element that meets at least one of the following requirements: the stabilizing element is constructed in such a way that it stabilizes at least portions of the guide element; the stabilizing element is made of plastic or metal; the stabilizing element is connected to the proximal end or a proximal end portion of the guide element; the stabilizing element is detachably connected to the guide element; the stabilizing element is uniformly connected with the guide element; the stabilizing element is glued or welded to the guide element; the stabilizing element is at least partially cylindrical; the stabilizing element is at least partially designed as a sleeve; the stabilizing element has at least in part an internal thread; the stabilizing element is at least partially pushed, plugged or screwed onto a proximal portion of the guide element.

A variety of cell types, molecules, and tumor and biomarkers are present in body fluids. However, it is often not possible to obtain them in sufficient quantity for analysis because they are present in very low concentrations. For diagnostic, prognostic, and scientific research purposes, these rare cells and other biomolecules are of high interest because they can serve as biomarkers of disease progression and diagnosis. For example, one of the leading causes of death worldwide is cancer. Breast, colon, prostate, gastric, hepatic, melanoma and lung tumors are the most common forms of cancer worldwide and in the United States. Having the ability to detect the development of cancer early in the disease process would have a significant impact on the health of the population.

The early spread of viable tumor cells and molecules are considered a hallmark of cancer progression. As a tumor grows, malignant cells may spread from their primary location to distant sites within the body. These malignant cells travel through body fluids such as blood or lymph. If cancer cells (e.g., circulating tumor cells (CTCs)) can be detected early in the disease process, then cancer and a disease relapse can be diagnosed and treated earlier and more effectively. Biomarkers in body fluids can also be measured periodically to monitor disease progression. However, because tumor and other disease biomarkers are often present in low concentrations, they cannot be efficiently recovered by conventional methods of enrichment for analysis by established diagnostic methods of clinical chemistry, pathology, or cytology, as well with imaging technology the tumor has to have a sufficient size to be detected As a result, a patient's disease may remain at a subclinical level for years before it is detected. New methods are needed to achieve early detection of occult cancer cells, which can result in early diagnosis, more aggressive treatment, and improved clinical outcomes. Other forms of blood biomarkers are circulating cancer cell free nucleic acids (e.g., DNA, RNA, microRNA).

Exosomes released from tumor cells and normal cells also detected in circulating form in body fluids. Exosomes are 30 to 200 nm, membrane-bound vesicles that are released by most types of cells, including tumor cells. Exosomes contain a great variety of bioactive molecules, including tumor marker peptides, microRNA, cell surface tumor antigens, mRNA, and DNA. In cancer, tumor cells aberrantly secrete large quantities of exosomes to transport paracrine signals or to contribute to tumor-environment interaction at a distant site. Detection and isolation can be problematic whereby using an in vivo catching device can capture and allow more exosome than traditional blood tube procurement and centrifugation separation techniques which limit type of exosomes isolated.

Other applications of some embodiments of the invention include collection of infection disease pathogens (virus, fungi, bacteria, parasites, and the like). One potential main application is diagnosis. Other applications include monitoring patients during therapy, or relapse after being clinically cured. Diagnosis can be important for individuals in some cases who are in contact with patients who have pathogenic infectious disease or exposed in the environment with pathogens present. The approach of assessing infectious disease pathogens can be applied to humans and animals. The latter can be quite important in large animal (4 legs) livestock used in the human consumption food chain. Identification of pathogen virus infection at early stages could be a very cost effective and treatment strategy. Early detection of low levels of pathogen in body fluids is limited by current conventional blood tube<10 ml assessment. The identification of a few infected animals at an early stage can prevent a "herd effect".

Examples of diagnostic approaches for identifying sepsis patients are generally based on either pathogen detection or evaluation of host response using biomarkers. The mainstay and de facto "gold standard" for diagnosis of most bacterial infections, including sepsis, is microbial growth of a causative pathogen followed by taxonomic identification. However, culture-based methods suffer from multiple limitations: (1) positive results usually take ≥24 h; (2) in clinically confirmed sepsis cases, positive cultures are produced in only ~⅓ of blood cultures and ~⅔ of all cultures from any site including blood, and, consequently, negative culture results cannot be interpreted definitively; (3) there is a reduced chance of positive culture if the patient is already on antibiotics; (4) interpretation is confounded by false positives produced by contaminants; and (5) positive blood cultures can result from transient bacteremia in the absence of a severe inflammatory response; (6) assessment of rare pathogens circulating at early stages to obtain sufficient amount for downstream assay analysis; (7) obtaining sufficient amount of pathogens to obtain enough sample of pathogen for multiple testing for identification. Thus, approaches by themselves have inadequate sensitivity, specificity, and predictive value for diagnosing sepsis.

Systemic inflammation is a whole body reaction having an infection-positive (e.g., sepsis) or infection-negative origin. It can be important to distinguish between these two etiologies early and accurately because this can have significant therapeutic implications for critically ill patients. Rapid diagnosis at the earliest stage can be effectively treatable thus some embodiments of the invention can identify at the earliest potential stage of pathogen infection without drawing any significant amount of blood. If bacterial DNA can be detected early in the disease process that can (1) determine which patients with systemic inflammation had sepsis, (2) be robust across independent patient cohorts, (3) be insensitive to disease severity, and (4) provide diagnostic utility.

Similar approaches to viral diseases can be highly advantageous if one can catch at very early stages in blood; thus more effective in treatment. Examples include rare HIV, Hepatitis virus, dengue virus, influenza virus, rotavirus, Lhassa, hantavirus, EBOLA virus, and other dangerous viruses. Early detection of rare presence of a virus would be very important in diagnosis and activation of immediate treatment. This would save morbidity and health care cost for assessing high risk patients. Also advantageous in some embodiments is diagnosis of a viral infection with sufficient virus pathogen to assess the infection. Identification and collection of patients with pulmonary pneumonia symptoms that need to be determined if bacterial or virus infection. Often problem is enough sample of blood for performing downstream identification assays rapidly before full blown infection occurs. Rapid decision for immediate therapeutic albeit antibiotic or viral targeted can be valuable.

Endothelial progenitor cells (EPCs) are a group of heterogeneous cell population capable of differentiating into the endothelial lineage. There is growing evidence that the dysfunction of EPCs is closely related to the development of many cardiovascular diseases, such as hypertension, hyperlipidemia, coronary heart disease and stroke. It is well recognized that vascular endothelial dysfunction is closely correlated with the development of hypertension. The factors accounting for endothelial dysfunction in hypertension are very complicated, but reduction in EPCs numbers and function is believed to play a key role in this regard. In patients with essential hypertension or in spontaneously hypertensive rats (SHR), the number of circulating EPCs is significantly decreased.

Assessment of acute chest pain is a frequent, time consuming clinical challenge. Approximately 30% of cases involve acute coronary syndromes (ACSs). Early diagnosis and appropriate treatment of patients are pivotal to avoid serious complications and death. On the basis of the ECG and clinical data, many non-ST-elevation ACSs are missed. An estimated 10% of ACS patients presenting in emergency rooms are mistakenly discharged, with an increased risk of progression to ST-elevation myocardial infarction or death.

Various laboratory markers of myocardial cell necrosis have been proposed to assist diagnostic and therapeutic decision making. These biomarkers include creatine phosphokinase of muscle band (CPK-MB) and troponins for myocardial necrosis, brain natriuretic peptide for left ventricular overload and C-reactive protein (CRP) for inflammation; however, these markers have several shortcomings. The diagnostic specificity of brain natriuretic peptide and CRP is low. Troponin levels remain low in many cases of non-ST-elevation ACS, and initial findings may be negative in some high-risk patients depending on the time of sampling, assay sensitivity, marker release, and clearance kinetics. These problems can delay proper diagnosis and care. The availability of a specific and early marker of non-ST-elevation ACS, the level of which becomes elevated before or in the absence of an elevation of troponin, might facilitate diagnosis and improve therapeutic decision making. ACSs usually result in coronary plaque rupture or erosion with endothelial disruption. Measurement of circulating endothelial cells (CECs) shed from damaged endothelium might provide a simple, noninvasive method to improve current diagnostic strategies.

Whereas CEC counts are very low in normal individuals, elevated counts have been documented in a variety of vascular disorders. An increased CEC level can be detected in patients with ACS and low numbers in subjects with effort angina or noncoronary chest pain. An elevation of CECs may identify a subgroup of ACS patients with an initially normal troponin level. The isolation of CECs from the peripheral blood thus can be an early, specific, independent diagnostic marker for non-ST-elevation ACS. CEC also assessed in neurostroke and kidney disease damage assessment.

Other applications include the detection of circulating free nucleic acids (cfNA) in the form of DNA, mRNA, histone bound DNA, and microRNA. Detection of these cancer specific or infectious disease related cfNA would allow early detection, monitoring patients being treated or non treated, identification of genotype changes in cancer or pathogen. Detection of cfNA can be by probe techniques such as peptide nucleic acid (PNA), BNA, LNA, XNA are for DNA and RNA hybridization, or related type DNA or peptide analogue probes or antibodies. The synthesis of PNA or related synthetic (LNA, BNA, XNA, aptamers) probes is flexible and the incorporation of chiral units along the carbon chains of the molecule backbone provide unique molecular configurations for the functional group and solid surface attachment. PNA probes which are bound to the collection device from PNA-DNA complementary duplexes according to Watson-Crick base pairing rules, have higher affinity and sequence selectivity compared to conventional DNA-DNA duplex hybridization.

In some embodiments, nucleosomes can also be detected using systems and methods as disclosed herein. The nucleosome is the basic unit of chromatin structure and consists of a protein complex of eight highly conserved core histones (comprising a pair of each of the histones H2A, H2B, H3, and H4). Around this complex is wrapped approximately 146 base pairs of DNA. Another histone, H1 or H5, acts as a linker and is involved in chromatin compaction. Status of histones methylation or acetylation can be assessed on isolation to determine disease related changes compared to normal. The DNA is wound around consecutive nucleosomes in a structure often said to resemble "beads on a string" and this forms the basic structure of open or euchromatin. In compacted or heterochromatin this string is coiled and super coiled into a closed and complex structure.

Methods currently exist to capture metastatic cells (CTC) and other biomarkers from body fluids. For example, the enrichment of specific cells, especially CTC, is possible from a blood sample of a patient using commercially available paramagnetic nanoparticles and/or density gradient centrifugation. One of these commercial methods is a test in which cells such as CTCs can be enriched from 7.5 ml of blood by paramagnetic nanoparticles, which enables observations about the disease process. However, the cells can only be collected in very limited quantities, which may be insufficient for analysis. Furthermore, the nanoparticles can irreversibly penetrate or bind to the cells, thereby contaminating the sample and affecting the diagnostic steps that follow the collection.

Alternatively, antibodies directed against a specific cell-surface marker can be covalently or otherwise coupled to a solid support which serves as a capturing device. Antibodies are large complex molecules that can be covalently attached to a binding surface such as beads by different types of chemistries. Most often lysine-based coupling is performed leading to unspecified and multiple attachment sites. Cleavage of the antibody by unspecified proteases is not possible since this would harm the cells of interest that are to be captured. Additionally, cells captured via such approaches bind tightly to the solid support of the capturing device, e.g. (magnetic) beads, foams, wire, polymers, etc. The gentle release of cells for further analysis (e.g. optical analysis in a two dimensional readout system) or proliferation is not possible due to the tight binding of multiple binding proteins to the cells. Furthermore, the constant part of antibodies can engage in cell contacts independent of the specificity of the variable domain directed against the specific cell surface marker and can lead to capturing of undesired cells, thus reducing the specificity of the cell capturing. The engineering and expression of antibodies can also be cumbersome and difficult.

In some embodiments, detection and/or collection systems as disclosed herein can include any number of the following features:

a wire comprising a functional member comprising a proximal end, a distal end, a first flat surface and a second flat surface opposing the first surface, the functional member configured to fit within a body lumen, wherein the functional member comprises binding elements configured to bind circulating biomaterials of interest, wherein the functional member comprises curved portions that form revolutions around the longitudinal axis of the device;

the wire comprises from about 3 revolutions to about 5 revolutions per 1 cm of length of the wire;

the wire comprises about 4 revolutions per 1 cm of length of the wire;
the wire comprises a metal;
the metal comprises stainless steel;
the metal comprises Nitinol;
a proximal handle that does not comprise binding elements;
an atraumatic distal end;
the functional member comprises a third surface and a fourth surface, the third surface and the fourth surface each adjacent the first surface and the second surface;
third surface and the fourth surfaces are flat surfaces, or not flat surfaces;
third surface and the fourth surfaces do not comprise binding elements;
a collar operably connected to the proximal end of the functional member, the collar configured to stably position the device within a body lumen;
the functional member has a non-circular, square, and/or rectangular cross-section;
a filter operably connected to the collar to isolate cells according to their size it also can change the blood flow;
binding elements comprise fusion proteins also biological probes or synthetic material probes;
functional member is coupled to a guidewire;
functional member is transformable from a first curved configuration to a second configuration more linear than the first configuration;
second configuration has a greater axial length than the first configuration;
at least part of the device is transformable from the second configuration to the first configuration via exposure to body temperature;
plurality of flaps operably connected to the distal end of the functional member;
flaps comprise apertures configured to filter blood;
a control line operably connected to the flaps;
flaps are movable between a first radially compressed configuration to a second radially expanded configuration;
functional member comprises a bifunctionally charged carrier;
control line runs at least partially through one or more eyelets on the functional member; and/or
control line runs at least partially through one or more apertures on the functional member;
functional surface/binding surface does not include an increased surface area (e.g., lacks pores and/or a microstructure);
functional surface/binding surface includes a smooth, uninterrupted, and/or continuous surface;
probe and/or wire segment includes, or does not include any of the following structures: a spiral, screw-shaped, worm-shaped, undulated, helical, filamentous, brush-like, comb-like, net-like, porous, spongy or similar structures.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "detecting and/or reversibly capturing cells, molecules, and other biomaterials from body fluids in vivo over time" includes "instructing the detecting and/or reversibly capturing cells, molecules, and other biomaterials from body fluids in vivo over time." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A biomaterial collection device, comprising:
a wire comprising a functional member comprising a proximal end, a distal end, a first flat surface, a second flat surface opposing the first flat surface, a third surface and a fourth surface each adjacent the first flat surface and the second flat surface, wherein the third surface and the fourth surface are curved surfaces, the functional member configured to fit within a body lumen, wherein the functional member comprises binding elements configured to bind circulating biomaterials of interest, wherein the third and fourth surfaces of the functional member form curved portions that form revolutions around the longitudinal axis of the device, wherein the wire comprises 9 revolutions per 1 cm of length of the wire.

2. The device of claim 1, wherein the wire comprises a metal.

3. The device of claim 2, wherein the metal comprises stainless steel.

4. The device of claim 2, wherein the metal comprises Nitinol.

5. The device of claim 1, further comprising a proximal handle that does not comprise binding elements.

6. The device of claim 1, wherein the wire comprises an atraumatic distal end.

7. The device of claim 1, wherein the third surface and the fourth surfaces do not comprise binding elements.

8. An in vivo biomaterial collection device, comprising:

a functional member comprising a proximal end, a distal end, a first flat surface, a second flat surface opposing the first flat surface, a third surface and a fourth surface each adjacent the first flat surface and the second flat surface, wherein the third surface and the fourth surface are curved surfaces, the functional member configured to fit within a body lumen, wherein the functional member comprises binding elements configured to bind circulating biomaterials of interest, wherein the third and fourth surfaces of the functional member form curved portions that form revolutions around the longitudinal axis of the device, wherein the wire comprises 8 revolutions per 1 cm of length of the wire.

9. The in vivo biomaterial collection device of claim 8, wherein the length of the first flat surface and the second flat surface is greater than the length of the third surface and the fourth surface.

10. The in vivo biomaterial collection device of claim 8, further comprising a filter operably connected to the collar to isolate cells according to their size, wherein the filter is configured to change the blood flow.

11. The in vivo biomaterial collection device of claim 8, wherein the binding elements comprise fusion proteins, biological probes, or synthetic material probes.

12. The in vivo biomaterial collection device of claim 8, wherein the functional member is coupled to a guidewire.

13. The in vivo biomaterial collection device of claim 12, wherein the guidewire comprises a metallic material.

14. The in vivo biomaterial collection device of claim 12, wherein the guidewire comprises a polymeric material.

15. An in vivo biomaterial collection device, comprising:

a functional member comprising a proximal end, a distal end, a first flat surface and a second flat surface opposing the first flat surface, a third surface and a fourth surface each adjacent the first flat surface and the second flat surface, wherein the third surface and the fourth surface are curved surfaces, the functional member configured to fit within a body lumen, wherein the functional member comprises binding elements configured to bind circulating biomolecules and cells, wherein the third and fourth surfaces of the functional member form curved portions that form revolutions around the longitudinal axis of the device, wherein the functional member is transformable from a first curved configuration to a second configuration more linear than the first configuration, wherein the functional member comprises 7 revolutions per 1 cm of length of the wire.

16. A biomaterial collection device, comprising:

a wire comprising a functional member comprising a proximal end, a distal end, a first flat surface, a second flat surface opposing the first flat surface, a third surface and a fourth surface each adjacent the first flat surface and the second flat surface, wherein the third surface and the fourth surface are curved surfaces, the functional member configured to fit within a body lumen, wherein the functional member comprises binding elements configured to bind circulating biomaterials of interest, wherein the third and fourth surfaces of the functional member form curved portions that form revolutions around the longitudinal axis of the device, wherein the wire comprises 10 revolutions per 1 cm of length of the wire.

\* \* \* \* \*